(12) United States Patent
Amano et al.

(10) Patent No.: US 8,105,770 B2
(45) Date of Patent: Jan. 31, 2012

(54) METHOD OF DETECTING AMPLIFICATION OR DELETION IN GENOMIC DNA FRAGMENT

(75) Inventors: Makoto Amano, Amagasaki (JP); Naoyuki Yamamoto, Amagasaki (JP)

(73) Assignee: Wako Pure Chemical Industries, Ltd., Osaka-shi (JP)

( * ) Notice: Subject to any disclaimer, the term of this patent is extended or adjusted under 35 U.S.C. 154(b) by 186 days.

(21) Appl. No.: 12/524,267

(22) PCT Filed: Jan. 28, 2008

(86) PCT No.: PCT/JP2008/051215
§ 371 (c)(1), (2), (4) Date: Jul. 23, 2009

(87) PCT Pub. No.: WO2008/102606
PCT Pub. Date: Aug. 28, 2008

(65) Prior Publication Data
US 2010/0112711 A1    May 6, 2010

(30) Foreign Application Priority Data

Jan. 31, 2007 (JP) ................................. 2007-020701

(51) Int. Cl.
*C12Q 1/68* (2006.01)
*C12P 19/34* (2006.01)
*G01N 33/00* (2006.01)
*B01L 3/00* (2006.01)
*C07H 21/00* (2006.01)
*C07H 21/02* (2006.01)

(52) U.S. Cl. ......... 435/6; 435/91.1; 435/91.2; 536/23.1; 536/24.3; 536/26.6; 422/68.1; 422/430

(58) Field of Classification Search ............ 435/6, 91.1, 435/91.2; 536/23.1, 24.3, 26.6; 422/430, 422/68.1
See application file for complete search history.

(56) References Cited

U.S. PATENT DOCUMENTS 6,083,485 A    7/2000    Licha et al.
(Continued)

FOREIGN PATENT DOCUMENTS

JP    7-505053 A    6/1995
(Continued)

OTHER PUBLICATIONS

Kallioniemi et al., Science, 258: 818-821 (Oct. 30, 1992).

*Primary Examiner* — Jezia Riley
(74) *Attorney, Agent, or Firm* — Leydig, Voit & Mayer, Ltd.

(57) ABSTRACT

[PROBLEMS] To provide a CGH method, in particular a CGH microarray method, enabling detection at an elevated accuracy and elevated sensitivity.
[MEANS FOR SOLVING PROBLEMS] A method which comprises: (a) labeling a test genomic DNA fragment that is a cell-origin genomic DNA fragment to be tested with either a label represented by the following general formula (1) or another label represented by the general formula (2), and labeling a control genomic fragment that serves as a standard for detecting a difference from the test genomic DNA fragment with the other label; (b) hybridizing the labeled test genomic DNA fragment and the labeled control genomic DNA fragment each with a specimen nucleic acid containing a nucleic acid sequence for detecting the difference between the test genomic fragment and the control genomic fragment; and (c) detecting an amplification or deletion in the test genomic DNA fragment by using the fluorescent intensities thus obtained as an indication; and a kit for the above-described method which contains a nucleotide residue labeled with the label represented by the following general formula (1) and a nucleotide residue labeled with the label represented by the following general formula (2).

12 Claims, 1 Drawing Sheet

U.S. PATENT DOCUMENTS

| | | |
|---|---|---|
| 6,258,340 B1 | 7/2001 | Licha et al. |
| 6,913,743 B2 | 7/2005 | Licha et al. |
| 6,926,885 B2 | 8/2005 | Licha et al. |
| 7,025,949 B2 | 4/2006 | Licha et al. |
| 2007/0048742 A1 | 3/2007 | Kang et al. |

FOREIGN PATENT DOCUMENTS

| | | |
|---|---|---|
| JP | 2005-304481 A | 11/2005 |
| JP | 2006-94726 A | 4/2006 |
| JP | 2006-115844 A1 | 5/2006 |
| WO | WO 93/18186 A1 | 9/1993 |
| WO | WO 96/17628 A1 | 5/1996 |

METHOD OF DETECTING AMPLIFICATION OR DELETION IN GENOMIC DNA FRAGMENT

TECHNICAL FIELD

The present invention relates to a comparative genomic hybridization method (CGH method), in particular, to a CGH microarray method using a microarray.

BACKGROUND ART

In recent years, the CGH method has been developed by Kallioniemi, et al. (Patent Literature 1, Non-patent Literature 1). This CGH method can detect copy number abnormality in genomic DNA of whole chromosome in a single hybridization, and has been widely exploited as a method for analyzing genomic aberration. The specific method is as follows. For example, at first, DNA extracted from a tumor tissue (cell) and DNA obtained from a normal tissue (cell) are each labeled with different fluorescent dye (for example, Cy3 and Cy5), and are allowed to hybridize competitively with a normal chromosome sample, and then the difference of fluorescent color of the chromosome is analyzed. In this instance, if amplification of gene/chromosome has occurred in the tumor tissue (cell), a normal chromosomal region corresponding to it will emit the fluorescent color originated from the DNA extracted from the tumor tissue (cell) strongly, because the normal chromosomal region could have hybridized with relatively large amount of DNA extracted from the tumor tissue (cell); on the contrary, when a deleted region of gene/chromosome is present in the tumor tissue (cell), a normal chromosomal region corresponding to it will emit the fluorescent color originated from DNA extracted from the normal tissue (cell) strongly [the fluorescent color originated from the tumor tissue (cell) will be emitted weakly], because the normal chromosomal region could have hybridized with relatively large amount of the DNA extracted from the normal tissue (cell). For this reason, from this hue, the region where the number of copy of the gene/chromosome in tumor tissue (cell) is out of balance can be detected as a position in the chromosome sample.

Furthermore, to perform this CGH method more simply yet quickly, as an alternative to the normal chromosome sample, the CGH microarray method employing a microarray which has been bound with DNA clone and cDNA covering whole chromosome region, oligonucleotide, and the like has been developed (Patent Literature 2, Patent Literature 3, and Patent Literature 4).

However, the above-described CGH method was not necessarily sufficient with respect to detection sensitivity and detection accuracy due to the fluorescent dye to be employed.

Patent Literature 1: JP-A-07-505053
Patent Literature 2: JP-A-2006-9115844
Patent Literature 3: JP-A-2006-94726
Patent Literature 1: JP-A-2005-304481
Non-patent Literature 1: Kallioniemi et al., Science, 258, p. 818-821, 1992.

DISCLOSURE OF INVENTION

Problem to be Solved by the Invention

The present invention has been made in view of the above mentioned situation, and an object of the present invention is to provide a CGH method, particularly a CGH microarray method, which can perform the detection with better accuracy and higher sensitivity.

Means for Solving the Problem

The present invention was made to solve the above-described problem, and comprises the following aspects.

1. A method for detecting amplification or deletion in a test genomic DNA fragment, comprising (a) labeling a test genomic DNA fragment which is a genomic DNA fragment derived from the objective cell to be inspected with either one of a labeling substance shown by the general formula (1) or a labeling substance shown by the general formula (2), and labeling a control genomic DNA fragment which is used as a standard for detecting difference from said test genomic DNA fragment with the other labeling substance; (b) competitively hybridizing the labeled test genomic DNA fragment and the labeled control genomic DNA fragment with a sample nucleic acid comprising a nucleotide sequence for detecting difference between the test genomic DNA fragment and the control genomic DNA fragment; and (c) detecting amplification or deletion in the test genomic DNA fragment by using the obtained fluorescence intensity as an indicator.

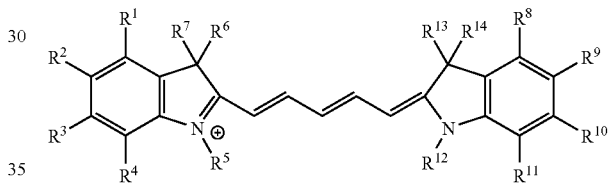

(1)

[Wherein, $R^1$-$R^4$ and $R^8$-$R^{11}$ represent independently from each other a hydrogen atom or —$SO_3R^{15}$ (wherein, $R^{15}$ represents a hydrogen atom, an alkali metal atom, an organic ammonium ion or an ammonium ion.), $R^5$ and $R^{12}$ represent independently from each other an alkyl group or a sulfoalkyl group, $R^6$, $R^7$, and $R^{14}$ represent independently from each other an alkyl group, and $R^{13}$ represents a carboxyalkyl group.]

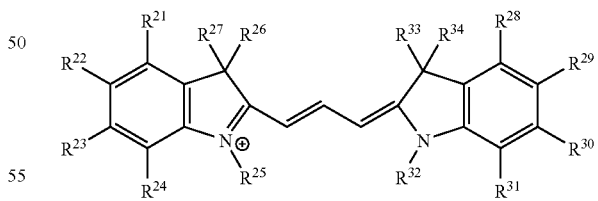

(2)

[Wherein, $R^{21}$-$R^{24}$ and $R^{28}$-$R^{31}$ represent independently from each other a hydrogen atom or —$SO_3R^{35}$ (wherein, $R^{35}$ represents a hydrogen atom, an alkali metal atom, an organic ammonium ion or an ammonium ion.), $R^{25}$ and $R^{32}$ represent independently from each other an alkyl group or a sulfoalkyl group, $R^{26}$, $R^{27}$ and $R^{34}$ represent independently from each other an alkyl group, and $R^{33}$ represents a carboxyalkyl group.]

2. A kit for the method according to the above item 1, comprising a nucleotide residue labeled with a labeling substance shown by the following general formula (1) and a nucleotide residue labeled with a labeling substance shown by the following general formula (2).

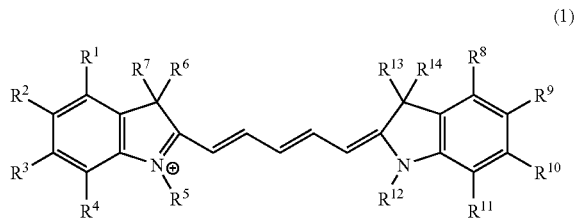

(1)

[Wherein, $R^1$-$R^4$ and $R^8$-$R^{11}$ represent independently from each other a hydrogen atom or —$SO_3R^{15}$ (wherein, $R^{15}$ represents a hydrogen atom, an alkali metal atom, an organic ammonium ion or an ammonium ion.), $R^5$ and $R^{12}$ represent independently from each other an alkyl group or a sulfoalkyl group, $R^6$, $R^7$ and $R^{14}$ represent independently from each other an alkyl group, and $R^{13}$ represents a carboxyalkyl group.]

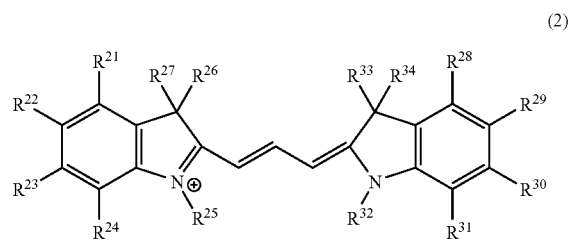

(2)

[Wherein, $R^{21}$-$R^{24}$ and $R^{28}$-$R^{31}$ represent independently from each other a hydrogen atom or —$SO_3R^{35}$ (wherein, $R^{35}$ represents a hydrogen atom, an alkali metal atom, an organic ammonium ion or an ammonium ion.), $R^{25}$ and $R^{32}$ represent independently from each other an alkyl group or a sulfoalkyl group, $R^{26}$, $R^{27}$ and $R^{34}$ represent independently from each other an alkyl group, and $R^{33}$ represents a carboxyalkyl group.]

Effect of the Invention

According to the method of the present invention, as compared with the conventional CGH method, especially with the CGH microarray method, the CGH analysis can be performed with better accuracy and higher sensitivity, i.e., copy number abnormality in a genomic DNA can be detected with high precision yet high sensitivity.

BEST MODE FOR CARRYING OUT THE INVENTION

1. CGH Method

In the present invention, the CGH method is, in principle, a method comprising (a) labeling a test genomic DNA fragment which is a genomic DNA fragment derived from an objective cell to be inspected and a control genomic DNA fragment which is used as a standard for detecting difference from the aforementioned test genomic DNA fragment with two types of labeling substances with different absorption wavelengths; (b) competitively hybridizing the labeled test genomic DNA fragment and the labeled control genomic DNA fragment with a sample nucleic acid comprising a nucleotide sequence for detecting difference between the test genomic DNA fragment and the control genomic DNA fragment; and (c) detecting copy number abnormality in the test genomic DNA (i.e. amplification or deletion in the test genomic DNA fragment) by using the obtained fluorescence intensity as an indicator.

On this occasion, detection of the copy number abnormality is carried out, usually, by measuring fluorescence intensity on the sample nucleic acid after competitive hybridization with the test genomic DNA fragment and the control genomic DNA fragment; then determining the fluorescence intensity ratio between a fluorescence intensity of the labeling substance derived from the test genomic DNA fragment and a fluorescence intensity of the labeling substance derived from the control genomic DNA fragment; and analyzing the fluorescence intensity ratio. Namely, when the ratio of fluorescence intensity of the labeling substance derived from the test genomic DNA fragment to the fluorescence intensity of the labeling substance derived from the control genomic DNA fragment is high, this indicates that the relevant part (region) in the sample nucleic acid has been hybridized more strongly with the test genomic DNA fragment as compared with the control genomic DNA fragment, and it may be judged that the region in the test genomic DNA corresponding to the relevant part (region) in the sample nucleic acid has been amplified (the copy number has been increased). On the contrary, when the ratio of the fluorescence intensity of the labeling substance derived from the test genomic DNA fragment to the fluorescence intensity of the labeling substance derived from the control genomic DNA fragment is low (or else, when the fluorescence of the labeling substance derived from the test genomic DNA fragment is not detected), this indicates that the relevant part (region) in the sample nucleic acid has been hybridized more strongly with the control genomic DNA fragment as compared with the test genomic DNA fragment (or else, only the control genomic DNA fragment has hybridized), and it may be judged that the region in the test genomic DNA corresponding to the relevant part (region) in the sample nucleic acid has been deleted (the copy number has been decreased, or else not copied). It should be noted that, in the present invention, judgment on the copy number abnormality (or chromosomal abnormality) in the test genomic DNA as described above, in other words, quantitative (or semi-quantitative) determination on the presence of the copy number abnormality (or chromosomal abnormality) in the test genomic DNA, or on the increased or decreased amount of the copy number is also included.

2. Method of the Present Invention

The present invention is characterized by employing the fluorescent substances shown by the general formula (1) and (2) as two types of labeling substances with different absorption wavelength used in the CGH method as mentioned above.

(1) Test Genomic DNA Fragment and Control Genomic DNA Fragment

In the present invention, the phrase "test genomic DNA fragment" means the genomic DNA derived from the objective cell to be inspected (to be detected and investigated for copy number abnormality or chromosomal aberration); in addition, the phrase "control genomic DNA fragment" means the genomic DNA fragment used as a standard for detecting difference from aforementioned test genomic DNA fragment (namely, copy number abnormality in the test genomic DNA).

In addition, the test genomic DNA fragment and the control genomic DNA fragment are each derived from different genomic DNA obtained from different biological sample, respectively. The different samples include, for example, (1) a case where the type of the samples are different, but the origin [living organism (individual or population), place, etc.] of the samples is identical, (2) a case where the type of samples are identical, but the origin of the samples is different, (3) a case where the type and origin of the samples are different, and (4) a case where the type and origin of the samples are identical.

In more specifically, for example, (1) different type of cell, cell population, body fluid and the like in the same individual (living organism, organism species), (2) the same type of cell, cell population, body fluid and the like between different individuals (living organism, organism species) [for example, between a specific individual and standard (normal) individual] or between the specific individual (living organism, organism species) and population [for example, between specific individual and standard (normal) population], (3) different type of cell, cell population, body fluid and the like [for example, abnormal cell (tissue, organ, body fluid) and normal cell (tissue, organ, body fluid) and the like] between different individuals (living organism, organism species) [for example, between a diseased individual and standard (normal) individual] or between specific individual (living organism, organism species) and population [between a diseased individual and standard (normal) population], and (4) the same type of cell, cell population, body fluid and the like in the same individual (living organism, organism species) under the different circumstances, condition and the like (for example, before and after drug administrations, before and after addition of stress, different stage of clinical condition, before and after cultivation and so on), are included.

It should be noted that, although the test genomic DNA fragment and the control genomic DNA fragment are the ones which comprise substantially the same nucleic acid (DNA) sequence, generally, the control genomic DNA fragment is a genomic DNA fragment obtained from a sample having no variation in copy number of genomic DNA (not having an abnormality in copy number of genomic DNA) [for example, standard (normal) individual or population, normal cell (tissue, organ, body fluid) and the like], in addition, the test genomic DNA fragment is a genomic DNA fragment obtained from a sample having variation in copy number of genomic DNA other than this (having an abnormality in copy number of genomic DNA) or else a sample suspected to have aforementioned variation (suspected to have aforementioned abnormality) [for example, specific individual, diseased individual, abnormal (tissue, organ, body fluid) and the like], however, they are not limited to such combinations.

In the test genome DNA fragment and the control genomic DNA fragment, for example, the genomic DNA fragment which has substantially the sequence corresponding to all chromosomes, for example, the genomic DNA fragment which has substantially the sequence corresponding to a specific chromosome, the genomic DNA fragment which has the sequence correspond to a part of these chromosomes (all chromosomes or specific chromosome), etc. are included. In addition, genomic DNA clone fragment, DNA fragment produced by fragmentation using restriction enzyme or chemically from these genomic DNA fragment or genomic DNA clone fragment, and the amplification products of these genomic DNA fragment, genomic DNA clone fragment or DNA fragment can also be used. Furthermore, cDNA, its DNA fragment, or these amplification products can also be used.

It should be noted that, generally, when one of both genomic DNA fragments is the one which has substantially the sequence corresponding to all chromosomes (or specific chromosome), the other also has substantially the sequence which corresponds to all chromosomes (or specific chromosome) similarly, and also, when one of both genomic DNA fragments is the one which has the sequence corresponding to a part of chromosome (all chromosomes or specific chromosome), the other has the sequence corresponding to the same part as aforementioned part of the chromosome (all chromosomes or specific chromosome).

The type of sample to which the present invention is applied may be the one commonly used in this field, and is not particularly limited. Such a sample includes, for example, biological samples such as cell, tissue, organ, and body fluid (blood, serum, plasma, cerebrospinal fluid, synovial fluid, pancreatic juice, lymph and the like), excretory substances (urine, saliva, fecal matter, etc.), expectorated sputum, pus, skin-derived substance and so on; microorganisms (fungi, bacteria, virus and the like); for example, environmental samples (foods, beverages, tap water, seawater, lake water, liver water, industrial effluent, rinse water for semiconductor, cleansing fluid after cleansing medical implements, etc.); extracted material obtained from them; processed substance obtained by dissolving these substances appropriately and reconstituted in water or buffer solution usually used in this field (Tris buffer, glycine buffer, phosphate buffer, veronal buffer, borate buffer, Good's buffer, etc.).

Such test genomic DNA fragment and control genomic DNA fragment can be prepared from the above-described samples using extraction method well known per se or a commercial extraction kit. In addition, depending on the purpose, it is also possible to use the commercially available genomic DNA fragments [for example, genomic DNA fragments (control genomic DNA fragments) derived from standard (normal) sample and genomic DNA fragments (test genomic DNA fragment) derived from a patient of a certain type of cancer].

In addition, method for preparation of genomic DNA clone fragment, method for preparation of cDNA, method for fragmentation by restriction enzyme, chemical fragmentation method, method for amplification (for example, amplification methods described in Genomics 87 (2006) 298-306, such as DOPPCR, rolling Cycle Amplification, and GenomePlex, ICAN method, LAMP method, and other methods capable of amplifying genome, etc.) and so on may also subject to the method well known per se or the commercially available kit.

(2) Labeling Substance

In the present invention, the labeling substances to be used for labeling the above-described test genomic DNA fragment and the control genomic DNA fragment are two types of fluorescent labeling substances shown by the following general formula (1) (hereinafter, abbreviated as labeling substance (1) involved in the present invention) and fluorescent labeling substance shown by the following general formula (2) (hereinafter, abbreviated as labeling substance (2) involved in the present invention).

(1)

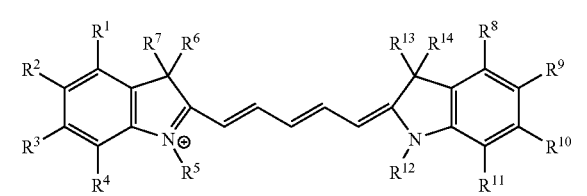

[Wherein, $R^1$-$R^4$ and $R^8$-$R^{11}$ represent independently from each other a hydrogen atom or —$SO_3R^{15}$ (wherein, $R^{15}$ represents a hydrogen atom, an alkali metal atom, organic ammonium ion or ammonium ion.), $R^5$ and $R^{12}$ represent independently from each other an alkyl group or a sulfoalkyl group, $R^6$, $R^7$, and $R^{14}$ represent independently from each other an alkyl group, and $R^{13}$ represents a carboxyalkyl group.]

It should be noted that, in the general formula (1), at least one of $R^1$-$R^4$ and $R^8$-$R^{11}$ is preferably —$SO_3R^{15}$ ($R^{15}$ is the same as described above), and may form salt with $N^+$ intramolecularly.

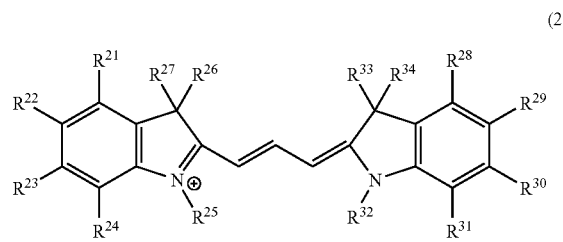

(2)

[Wherein, $R^{21}$-$R^{24}$ and $R^{28}$-$R^{31}$ represent independently from each other a hydrogen atom or —$SO_3R^{35}$ (wherein, $R^{35}$ represents a hydrogen atom, an alkali metal atom, organic ammonium ion or ammonium ion.), $R^{25}$ and $R^{32}$ represent independently from each other an alkyl group or a sulfoalkyl group, $R^{26}$, $R^{27}$ and $R^{34}$ represent independently from each other an alkyl group, and $R^{33}$ represents a carboxyalkyl group.]

It should be noted that, in the general formula (2), at least one of $R^{21}$-$R^{24}$ and $R^{28}$-$R^{31}$ is preferably —$SO_3R^{35}$ ($R^{35}$ is the same as described above), and may form salt with $N^+$ intramolecularly.

In the above-described general formula (1) and (2), as to —$SO_3R^{15}$ and —$SO_3R^{35}$ shown by $R^1$, $R^2$, $R^3$, $R^4$, $R^8$, $R^9$, $R^{10}$, $R^{11}$, $R^{21}$, $R^{22}$, $R^{23}$, $R^{24}$, $R^{28}$, $R^{29}$, $R^{30}$, and $R^{31}$, an alkali metal atom shown by $R^{15}$ and $R^{35}$ includes, for example, sodium, potassium, lithium, etc., and among them, lithium and sodium are preferable.

The organic ammonium ion includes, for example, trialkylammonium ion and the like. In addition, aforementioned trialkylammonium ion may be any of straight chained, branched or cyclic and includes one having usually 1-10 carbon atoms, preferably 1-6 carbon atoms; and specifically, for example, trimethylammonium ion, triethylammonium ion, tri-n-propylammonium ion, triisopropylammonium ion, tributylammonium ion, trihexylammonium ion, trioctylammonium ion, trinonylammonium ion, tridecylammonium ion, tricyclopentylammonium ion, tricyclohexylammonium ion, tricycloheptylammonium ion, tricyclooctylammonium ion, etc. are included. Among them, trimethylammonium ion or triethylammonium ion is preferable, and triethylammonium ion is more preferable.

The alkyl group shown by $R^5$, $R^6$, $R^7$, $R^{12}$, $R^{14}$, $R^{25}$, $R^{26}$, $R^{27}$, $R^{32}$, and $R^{34}$ may be any of straight chained, branched or cyclic and includes one having usually 1-6 carbon atoms, preferably 1-3 carbon atoms; and specifically, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a cyclopropyl group, a cyclobutyl group, a cyclopentyl group, a cyclohexyl group, etc. are included. Among them, straight chained alkyl groups such as a methyl group, an ethyl group and a n-propyl group are preferable.

The sulfoalkyl group shown by $R^5$, $R^{12}$, $R^{25}$, and $R^{32}$ is an alkyl group having a sulfo group, and usually 1-10 carbon atoms, preferably 1-6 carbon atoms. Such alkyl group may be any of straight chained, branched or cyclic, and for example, an ethyl group, a n-propyl group, an isopropyl group, a n-butyl group, an isobutyl group, a sec-butyl group, a tert-butyl group, etc. are included.

In addition, specific example of the sulfoalkyl group includes, for example, a sulfoethyl group, a sulfopropyl group, a sulfobutyl group, a sulfopentyl group, a sulfohexyl group, etc., and preferably a 2-sulfoethyl group, a 3-sulfopropyl group, and a 4-sulfobutyl group are included.

The carboxyalkyl group shown by $R^{13}$ and $R^{33}$ is an alkyl group having usually 1-3 carboxy groups, preferably 1 carboxy group, and having usually 1-10 carbon atoms, preferably 1-6 carbon atoms. Such alkyl group may be any of straight chained, branched or cyclic, and for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a cyclopropyl group, a cyclobutyl group, a cyclopentyl group, a cyclohexyl group, etc. are included. Among them, the one having a straight chained alkyl group is preferable.

In addition, specific example of the carboxyalkyl group includes, for example, a carboxymethyl group, a carboxyethyl group, a carboxypropyl group, a carboxybutyl group, a carboxypentyl group, a carboxyhexyl group, a 1,2-dicarboxyethyl group, a 1,3-dicarboxypropyl group, a 3,5-dicarboxyphenyl group, a 3,4-dicarboxyphenyl group, a 2,4-dicarboxyphenyl group, a 4-(1,2-dicarboxyethyl)-phenyl group, etc., and preferably includes a carboxymethyl group, a 2-carboxyethyl group, a 3-carboxypropyl group, a 4-carboxybutyl group, a 5-carboxyhexyl group, etc. More preferable carboxyalkyl groups are a 2-carboxyethyl group, a 3-carboxypropyl group, and a 4-carboxybutyl group.

Specific example of preferable labeling substance (1) involved in the present invention includes, for example, the ones shown in the following table.

| | $R^1$ | $R^2$ | $R^3$ | $R^4$ | $R^5$ | $R^6$ | $R^7$ | $R^8$ | $R^9$ | $R^{10}$ | $R^{11}$ | $R^{12}$ | $R^{13}$ | $R^{14}$ |
|---|---|---|---|---|---|---|---|---|---|---|---|---|---|---|
| (1)-1 | H | —$SO_3Na$ | H | H | —$CH_2CH_3$ | —$CH_3$ | —$CH_3$ | H | —$SO_3Na$ | H | H | —$CH_2CH_3$ | —$(CH_2)_3COOH$ | —$CH_3$ |
| (1)-2 | H | —$SO_3Na$ | H | H | —$CH_3$ | —$CH_3$ | —$CH_3$ | H | —$SO_3Na$ | H | H | —$CH_3$ | —$(CH_2)_3COOH$ | —$CH_3$ |
| (1)-3 | H | —$SO_3Na$ | H | H | —$(CH_2)_3SO_3$ | —$CH_3$ | —$CH_3$ | H | —$SO_3Na$ | H | H | —$CH_2CH_3$ | —$(CH_2)_3COOH$ | —$CH_3$ |
| (1)-4 | H | —$SO_3Na$ | H | H | —$CH_2CH_3$ | —$CH_3$ | —$CH_3$ | H | —$SO_3Na$ | H | H | —$CH_2CH_3$ | —$(CH_2)_6COOH$ | —$CH_3$ |

Specific example of preferable labeling substance (2) involved in the present invention includes, for example, the ones shown in the following table.

| | $R^{21}$ | $R^{22}$ | $R^{23}$ | $R^{24}$ | $R^{25}$ | $R^{26}$ | $R^{27}$ | $R^{28}$ | $R^{29}$ |
|---|---|---|---|---|---|---|---|---|---|
| (2)-1 | H | —SO$_3$Na | H | H | —CH$_2$CH$_3$ | —CH$_3$ | —CH$_3$ | H | —SO$_3$Na |
| (2)-2 | H | —SO$_3$Na | H | H | —CH$_3$ | —CH$_3$ | —CH$_3$ | H | —SO$_3$Na |
| (2)-3 | H | —SO$_3$Na | H | H | —(CH$_2$)$_3$SO$_3$ | —CH$_3$ | —CH$_3$ | H | —SO$_3$Na |
| (2)-4 | H | —SO$_3$Na | H | H | —CH$_2$CH$_3$ | —CH$_3$ | —CH$_3$ | H | —SO$_3$Na |

| | $R^{30}$ | $R^{31}$ | $R^{32}$ | $R^{33}$ | $R^{34}$ |
|---|---|---|---|---|---|
| (2)-1 | H | H | —CH$_2$CH$_3$ | —(CH$_2$)$_3$COOH | —CH$_3$ |
| (2)-2 | H | H | —CH$_3$ | —(CH$_2$)$_3$COOH | —CH$_3$ |
| (2)-3 | H | H | —CH$_2$CH$_3$ | —(CH$_2$)$_3$COOH | —CH$_3$ |
| (2)-4 | H | H | —CH$_2$CH$_3$ | —(CH$_2$)$_6$COOH | —CH$_3$ |

As for combination of the labeling substance (1) and the labeling substance (2) involved in the present invention, a combination in which both substances have the same substituent is preferable, specifically for example, a combination of (1)-1 and (2)-1 of the above table, a combination of (1)-2 and (2)-2, a combination of (1)-3 and (2)-3, a combination of (1)-4 and (2)-4, and the like are more preferable, and a combination of (1)-1 and (2)-1 is particularly preferable.

It should be noted that, the labeling substances (1) and (2) involved in the present invention can be synthesized by the method well known per se, for example, by the method described in WO96/17628 pamphlet (JP-A-2002-12782), U.S. Pat. No. 6,974,873, etc.

In addition, a commercial product [for example, DY-647 and DY-547, produced by DYOMICS (Dyomics GmbH)] can also be used.

(3) Labeled Test Genomic DNA Fragment, Labeled Control Genomic DNA Fragment and Labeling Method As mentioned above, the method of the present invention is the one which, in the CGH method, employs a test genomic DNA fragment labeled with either one of labeling substance (1) or labeling substance (2) (hereinafter, abbreviated as labeled test genomic DNA fragment) and a control genomic DNA fragment labeled with the other labeling substance (hereinafter, abbreviated as labeled control genomic DNA fragment).

In the present invention, the labeled test genomic DNA fragment is the one in which either one of labeling substance of the labeling substance (1) or the labeling substance (2) has been labeled to the test genomic DNA fragment directly or indirectly through a linker and the like, and also, the labeled control genomic DNA fragment is the one in which the other labeling substance of the labeling substance (1) or the labeling substance (2) (namely, the rest of the labeling substance (1) and the labeling substance (2) of the present invention other than the labeling substance used for labeling the test genomic DNA fragment) has been labeled to the above-described control genomic DNA fragment directly or indirectly through a linker and the like.

Specifically, these labeled test genomic DNA fragment and the labeled control genomic DNA fragment are the ones in which the carboxyalkyl group [$R^{13}$ in the general formula (1)] in the labeling substance (1) involved in the present invention or the carboxyalkyl group [$R^{33}$ in the general formula (2)] in the labeling substance (2) involved in the present invention are labeled to the test genomic DNA fragment or the control genomic DNA fragment directly or indirectly through a linker and the like.

Among others, for the labeled test genomic DNA fragment and the labeled control genomic DNA fragment to be employed in the present invention, the ones in which the carboxyalkyl group [$R^{13}$ in the general formula (1)] in the labeling substance (1) involved in the present invention or the carboxyalkyl group [$R^{33}$ in the general formula (2)] in the labeling substance (2) involved in the present invention are labeled to the test genomic DNA fragment or the control genomic DNA fragment indirectly through a linker and the like are preferable.

In the above description, although any of linkers usually used in this field can be employed, specifically, the linker having the structure shown below by general formula (A) is included.

-E-X-T-Y—NH   (A)

(Wherein, E represents —CH═CH— or —C≡C—; X and Y represent independently from each other an alkylene group; and T represents —O— or —NH—CO—.)

In the above-described general formula (A), the alkylene group shown by X may be any of straight chained, branched or cyclic, and includes the one having usually 1-10 carbon atoms, preferably 1-6 carbon atoms, more preferably 1-3 carbon atoms; and specifically, a straight chained alkylene group such as, for example, a methylene group, an ethylene group, a trimethylene group, a tetramethylene group, a pentamethylene group, a hexamethylene group, a heptamethylene group, an octamethylene group, a nonamethylene group and a decamethylene group; a branched alkylene group such as, for example, an ethylidene group, a propylene group, an isopropylidene group, a 1-methyltrimethylene group, a 2-methyltrimethylene group, a 1,1-dimethylethylene group, a 1,2-dimethylethylene group, an ethylethylene group, a 1-methyltetramethylene group, a 1,1-dimethyltrimethylene group, a 2,2-dimethyltrimethylene group, a 2-ethyltrimethylene group, a 1-methylpentamethylene group, a 1-methylhexamethylene group, a 1-methylheptamethylene group, a 1,4-diethyltetramethylene group, a 2,4-dimethylheptamethylene group, a 1-methyloctamethylene group, and a 1-methylnonamethylene group, a cyclic alkylene group such as, for example, a cyclopropylene group, a 1,3-cyclobutylene group, a 1,3-cyclopentylene group, a 1,4-cyclohexylene group, a 1,5-cycloheptylen group, a 1,5-cyclooctylene group, a 1,5-cyclononylene group, a 1,6-cyclodecalene group and the like are included. Among them, the straight chained alkylene groups are preferable.

The alkylene group shown by Y may be any of straight chained, branched or cyclic, and includes the one having usually 1-10 carbon atoms, preferably 2-8 carbon atoms, more preferably 2-6 carbon atoms; and specifically, a straight chained alkylene group such as, for example, a methylene group, an ethylene group, a trimethylene group, a tetramethylene group, a pentamethylene group, a hexamethylene group, a heptamethylene group, an octamethylene group, a nonamethylene group and a decamethylene group, a branched alkylene group such as, for example, an ethylidene group, a propylene group, an isopropylidene group, a 1-methyltrimethylene group, a 2-methyltrimethylene group, a 1,1-dimethylethylene group, a 1,2-dimethylethylene group, an ethylethylene group, a 1-methyltetramethylene group, a 1,1-dimethyltrimethylene group, a 2,2-dimethyltrimethylene group, a 2-ethyltrimethylene group, a 1-methylpentamethylene group, a 1-methylhexamethylene group, 1-methylheptamethylene group, a 1,4-diethyltetramethylene group, a 2,4-dimethylheptamethylene group, a 1-methyloctamethylene group, and a 1-methylnonamethylene group, a cyclic alkylene group such as, for example, a cyclopropylene group, a 1,3-cyclobutylene group, a 1,3-cyclopentylene group, a 1,4-cyclohexylene group, a 1,5-cycloheptylen group, a 1,5-cyclooctylene group, a 1,5-cyclononylene group, a 1,6-cyclodecalene group and the like are included. Among them, the straight chained alkylene groups are preferable.

Although the labeled test genomic DNA fragment and the labeled control genomic DNA fragment to be employed in the present invention are as described above, in other words, the labeled test genomic DNA fragment is the one which comprises either the nucleotide residue labeled with the labeling substance (1) involved in the present invention directly or indirectly through a linker and the like or the nucleotide residue labeled with the labeling substance (2) involved in the present invention directly or indirectly through a linker and the like, in addition, the labeled control genomic DNA fragment is the one which comprises the other nucleotide residue.

Among others, as for these labeled test genomic DNA fragment and the labeled control genomic DNA fragment, the one which comprises the nucleotide residue labeled with the labeling substance (1) or (2) involved in the present invention indirectly through a linker and the like is preferable.

More specifically, as for the labeled test genomic DNA fragment, the one which comprises either one of nucleotide residues shown by the following general formula (3) or general formula (4) is preferable, and also, as for the labeled control genomic DNA fragment, the one which comprises remaining the other nucleotide residue is preferable.

Q1-V1-W1 (3)

[Wherein, Q1 represents a nucleotide residue; V1 represents a linker; and W1 represents the following general formula (1').

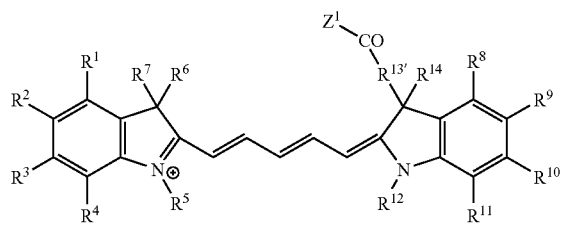

(1')

(Wherein, Z1 represents a joint for binding with V1; $R^{13'}$ represents an alkylene group; and $R^1$-$R^{12}$ and $R^{14}$ are the same as described above.)],

Q2-V2-W2 (4)

[Wherein, Q2 represents a nucleotide residue; V2 represents a linker; and W2 represents the following general formula (2').

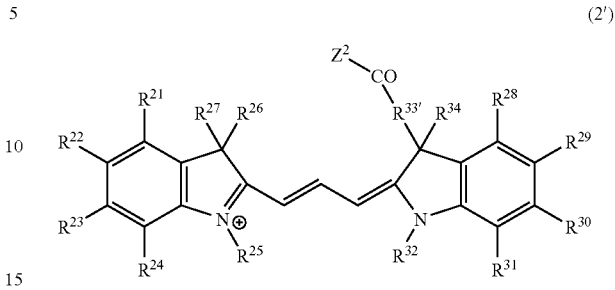

(2')

(Wherein, $Z^2$ represents a joint for binding with V2; $R^{33'}$ represents an alkylene group; and $R^{21}$-$R^{32}$ and $R^{34}$ are the same as described above)].

The nucleotide residue shown by Q1 and Q2 in the general formulas (3) and (4), respectively, includes, for example, a ribonucleotide residue, a 2'-deoxyribonucleotide residue, a 3'-deoxyribonucleotide residue, a 5'-deoxyribonucleotide residue, and a 2',3'-dideoxyribonucleoside, and so on.

Specifically, such a nucleotide residue includes, for example, purine nucleotide residues shown by the general formulas (i), (ii), (v), (vi), (vii), (viii), (xii), and (xiii) or pyrimidine nucleotide residues shown by the general formulas (iii), (iv), (x), and (xi).

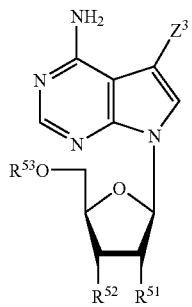

(i)

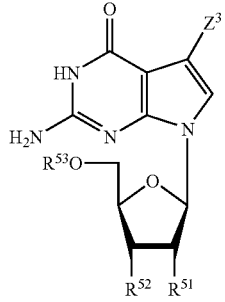

(ii)

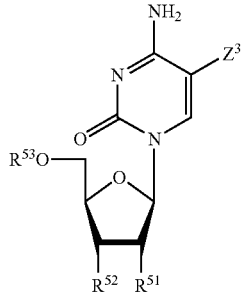

(iii)

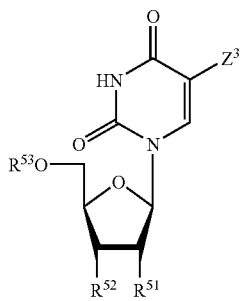
(iv)
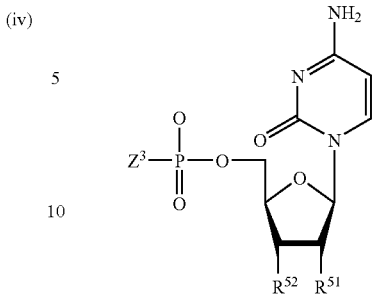
(ix)
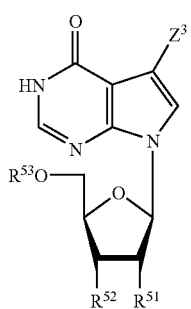
(v)
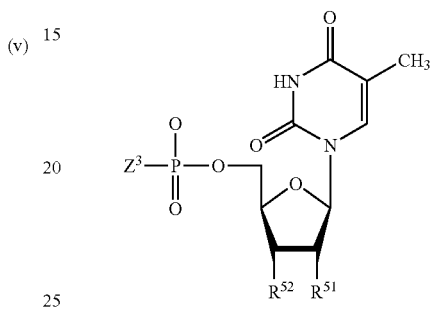
(x)
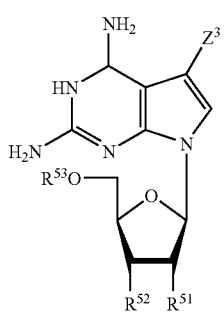
(vi)
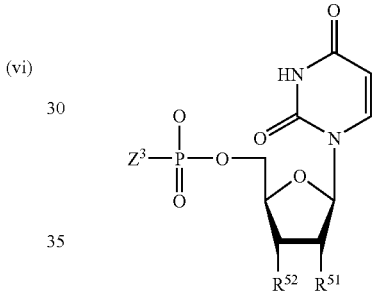
(xi)
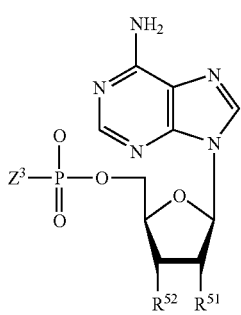
(vii)
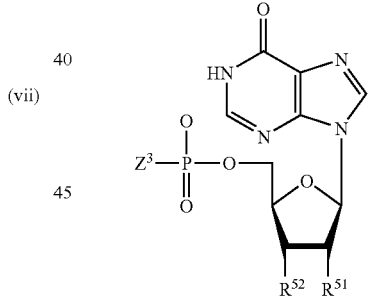
(xii)
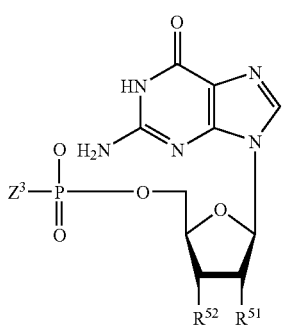
(viii)
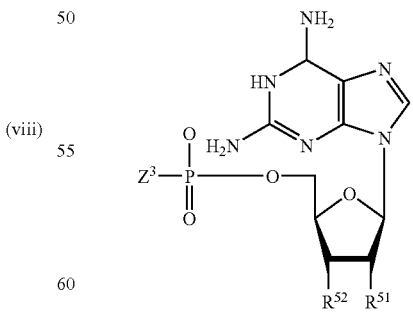
(xiii)
In the above-described general formulas, $Z^3$ represents a joint for binding with V1 or V2; each $R^{51}$ and $R^{52}$ represents independently from each other H, OH, or O—; and $R^{53}$ represents —PO$_2$H—, —PO$_3$H$_2$, —P$_2$O$_6$H$_3$ and —P$_3$O$_9$H$_4$ or salt thereof. In this regard, specific example of the salt includes an alkaline metal salt such as, for example, a sodium salt, a potassium salt and a lithium salt, and an organic amine salt such as, for example, an ammonium salt, a triethylammonium salt, and a pyridine salt, and the like.

In this respect, as for $R^{51}$ and $R^{52}$, a combination in which $R^{51}$ is H and $R^{52}$ is OH or O—, a combination in which both $R^{51}$ and $R^{52}$ are H, and a combination in which $R^{51}$ is OH and $R^{52}$ is H, OH or O— are preferable, and a combination in which $R^{51}$ is H and $R^{52}$ is OH or O— is more preferable.

In addition, $R^{53}$ is preferably —PO$_2$H— or —PO$_3$H$_2$.

It should be noted that, when the nucleotide residue shown by general formula (3) and (4) is used as a labeled mononucleotide for use in the method for enzymatic labeling of DNA fragment by using a labeled mononucleotide as described hereinafter, the nucleotides residue shown by Q1 and Q2 is preferably the one selected from general formulas (i)-(vi). In addition, as for $R^{51}$ and $R^{52}$ in general formulas (i)-(vi), a combination in which $R^{51}$ is H and $R^{52}$ is OH, and a combination in which both $R^{51}$ and $R^{52}$ are OH are preferable, and a combination in which $R^{51}$ is H and $R^{52}$ is OH is more preferable. Furthermore, as for $R^{53}$, —P$_3$O$_9$H$_4$ is preferable.

In the general formulas (3) and (4), the linker shown by V1 and V2 is the linker for connecting the nucleotide residue shown by Q1 and Q2 with the fluorescent label shown by W1 [general formula (1')] and W2 [general formula (2')].

That is, as for the pyrimidine nucleotide residue among nucleotide residues shown by the above-described Q1 and Q2, one terminus of the aforementioned linker is bound to the 5th position of the pyrimidine ring [in case of general formulas (iii) and (iv)] or a phosphorus atom of the phosphate residue [in case of general formulas (x) and (xi)], and also, as for the purine nucleotides residue, bound to the 7th position of the 7-deazapurine ring [in case of general formulas (i), (ii), (v) and (vi)] or a phosphorus atom of the phosphate residue of the purine ring (or 7-deazapurine ring) [in case of general formulas (vii), (viii), (ix), (xii), and (xiii)].

Further, the other terminus of the aforementioned linker is bound to the carbonyl group [a carbonyl group binding with $R^{13'}$ in the general formula (1'), a carbonyl group binding with $R^{33'}$ in the general formula (2')] of the labeling substances shown by W1 [general formula (1')] and W2 [general formula (2')].

As for such a linker, any of linkers which is capable of connecting the carbonyl group [a carbonyl group binding with $R^{13}$ in the general formula (1'), a carbonyl group binding with $R^{33}$ in the general formula (2')] of the labeling substance shown by W1 [general formula (1')] and W2 [general formula (2')] with the nucleotide residues shown by Q1 and Q2 can be utilized, and specifically, the linker of the structure shown by the following general formula (A) is included.

E-X-T-Y—NH (A)

Wherein, E, X, T, and Y are the same as described above, and specific examples and preferable examples thereof are the same as described above.

Therefore, as for the nucleotide residue shown by the general formula (3) and the general formula (4), the one which is shown in the following general formula (3') or (4'), respectively, is preferable, and the one which is shown by the following general formula (3") or (4") is more preferable.

Q1-E1-X1-T1-Y1-NH—W1 (3')

Q2-E2-X2-T2-Y2-NH—W2 (4')

(Wherein, E1 and E2 represent independently from each other —CH=CH— or —C≡C—; X1, X2, Y1, and Y2 represent independently from each other an alkylene group; and T1 and T2 represent independently from each other —O— or —NH—CO—. Further, Q1, Q2, W1, and W2 are the same as described above.)

In addition, in the foregoing, the alkylene groups shown by X1 and X2 are the same as the alkylene group shown by the aforementioned X, and its specific example and preferable example, etc. are also the same. Moreover, the alkylene groups shown by Y1 and Y2 are the same as the alkylene groups shown by the above-described Y, and its specific example and its preferable example, etc. are also the same.

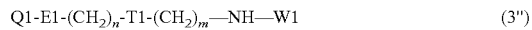

Q1-E1-(CH$_2$)$_n$-T1-(CH$_2$)$_m$—NH—W1 (3")

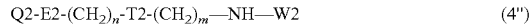

Q2-E2-(CH$_2$)$_n$-T2-(CH$_2$)$_m$—NH—W2 (4")

(Wherein, n represents an integer of 1-10, preferably of 1-6, more preferably of 1-4, and m represents an integer of 1-10, preferably of 2-8, more preferably of 2-4. Further, Q1, Q2, W1, W2, E1, E2, T1, and T2 are the same as described above.)

The alkylene group shown by $R^{13'}$ and $R^{33'}$ in the general formulas (1') and (2') is an alkylene group having usually 1-9 carbon atoms, preferably 1-5 carbon atoms. Such alkylene group may be any of straight chained, branched or cyclic, and includes, for example, a methylene group, an ethylene group, a n-propylene group, an isopropylene group, a n-butylene group, an isobutylene group, a sec-butylene group, a tert-butylene group, a n-pentylene group, an isopentylene group, a sec-pentylene group, a tert-pentylene group, a neopentylene group, a n-hexylene group, an isohexylebe group, a sec-hexylene group, a tert-hexylene group, a neohexylene group, a cyclopropylene group, a cyclobutylene group, a cyclopentylene group, a cyclohexylene group, etc. Among them, the straight chained alkyl alkylene group is preferable.

In addition, $R^1$-$R^{12}$, $R^{14}$, $R^{21}$-$R^{32}$ and $R^{34}$ are the same as described above, and specific example and preferable example thereof and the like are also the same as described above.

Such labeling substances shown by W1 [general formula (1')] and W2 [general formula (2')] are each derived from the above-described labeling substance (1) [general formula (1)] and labeling substance (2) [general formula (2)] involved in the present invention, and specific preferable examples thereof are also the same as the above described labeling substance (1) and the labeling substance (2) involved in the present invention.

As for the method for labeling the test genomic DNA fragment and the control genomic DNA fragment with the labeling substance (1) or the labeling substance (2) involved in the present invention as described above, any of methods which provide finally the test genomic DNA fragment comprising either one of the nucleotide residue labeled with the labeling substance (1) involved in the present invention directly or indirectly through a linker and the like or the nucleotide residue labeled with the labeling substance (2) involved in the present invention directly or indirectly through a linker and the like, and the control genomic DNA fragment comprising the remaining nucleotide residue can be employed.

Such labeling method includes the direct labeling method and the indirect labeling method well known per se [for example, the methods described in WO96/17628 (JP-A-2002-12782), U.S. Pat. No. 6,974,873, JP-A-2002-193991, WO99/12544, and JP-A-11-80189, and so on].

In addition, (1) a method for labeling DNA fragment enzymatically by using a labeled mononucleotide bound with labeling substance [for example, primer extension method (random primer method, primer method and the like), nick translation method, terminal addition reaction method (terminal deoxytransferase method and the like), PCR method, Degenerate Oligonucleotide Primer PCR (DOP-PCR) method etc.] and the like, (2) a method for labeling DNA fragment enzymatically by using labeled oligonucleotide bound with labeling substance as a primer [for example, primer extension method (random primer method, primer method and the like), PCR method, Degenerate Oligonucleotide Primer PCR (DOP-PCR) method etc.], and (3) a method for labeling DNA fragment in which labeled oligo- or polynucleotide is bound enzymatically with the DNA fragment [terminal addition reaction method (ligation method) and the like] can also be used.

Furthermore, the labeling may be carried out by the method in which after introducing a reactive group (for example, an aminoallyl group, a sulfhydryl group, etc.) into DNA fragment, this reactive group and labeling substance are bound, or by the method in which after introducing a physiologically active substance [for example, biotin, DIG (digoxigenin), sugar chain etc.] into DNA fragment, the aforementioned physiologically active substance is bound with a substance which has been bound with labeling substance and is capable of binding with the aforementioned physiologically active substance (for example, avidin, specific antibody, lectin, etc.).

It should be noted that, the above-described methods have been described, for example, in WO93/018186 (JP-A-07-505053), JP-A-2006-115844, JP-A-2005-304481, JP-A-2006-94726, JP-A-11-258233, JP2595201, and Nucleic Acids Research vol. 14, No. 19, p7617, 1986.

In addition, on the occasion of labeling the test genomic DNA fragment and the control genomic DNA fragment with the labeling substances (1) or (2) involved in the present invention, use of a commercially available labeling kit based on the above-described labeling method except for using the labeling substance (1) and (2) involved in the present invention would make it more simple and easy.

Among the above-described labeling methods, the method for labeling DNA fragment enzymatically by using labeled mononucleotide is preferable, and the random primer method, the nick translation method, and the terminal addition reaction method are more preferable.

In addition, in the present invention, in order to utilize these methods, the labeled mononucleotide bound with the labeling substance (1) involved in the present invention and the labeled mononucleotide bound with the labeling substance (2) involved in the present invention are required, but these labeled nucleotide can be prepared by the method well known per se (for example, the above-described labeling methods).

Specifically, according to the method described, for example, in JP-A-2002-193991 (paragraph: [0102]-[0121]), these can be prepared, for example, as follows.

That is, this can be achieved easily by reacting a nucleotide derivative shown by the following general formula (a) with a succinimidyl ester of the labeling substance (1) or (2) involved in the present invention shown by the following general formula (b).

Q-E-X-T-Y—NH$_2$ (a)

(Wherein, Q represents Q1 or Q2; Q1, Q2, E, X, T, and Y are the same as described above.)

W—OSu (b)

(Wherein, W represents W1 or W2; Su represents a succinimide group; W1 and W2 are the same as described above.)

In addition, when T (namely, T1 and T2) of the linker part shown by the general formula as described above is —NH—CO—, it can also be prepared, for example, as follows.

That is, this can be obtained easily, for example, firstly introducing a part of the linker (partial linker A) shown by the following general formula (c) and reacting the succinimidyl ester of the remaining part of the linker (partial linker B) to prepare the nucleotide derivative shown by the following general formula (d) into which the linker has been introduced is prepared, then reacting the nucleotide derivative shown by the following general formula (d) with the succinimidyl ester of the labeling substances (1) or (2) involved in the present invention shown by the following general formula (e).

-E-X—NH$_2$ (c)

(Wherein, E and X are the Same as Described Above.)

Q-E-X—NH—CO—Y—NH$_2$ (d)

(Wherein, Q, E, X and Y are the Same as Described Above.)

W—OSu (e)

(Wherein, W and Su are the Same as Described Above.)

More specifically, among the labeled mononucleotides bound with the above-described labeling substance (1) or the labeling substance (2) involved in the present invention, the fluorescence label of 2'-deoxycytidine-5'-triphosphate derivative and the fluorescence label of 2'-deoxyuridine-5'-triphosphate derivative may be synthesized, for example, according to the synthesis route as described below.

It should be noted that, abbreviated formal names used in the following synthesis routes are as follows.
MeOTfa: methyl trifluoroacetate
-Tfa: trifluoroacetyl group
Bu$_3$SnH: tri(n-butyl)tin hydride
AIBN: azoisobutyronitrile
Et$_3$N: triethylamine
HO-Su: N-hydroxy succinimide
DMF: N,N-dimethylformamide
TMS-Acetamide: N,O-bis(trimethylsilyl)acetamide
PdCl$_2$(CH$_3$CN)$_2$: bis(acetonitrile)dichloropalladium (II)
tris(TBAPP): tris(tri-n-butylammonium) pyrophosphate
(EtO)$_3$PO: triethyl phosphate
TFP: tri-2-fryl phosphine
Pd$_2$(dba)$_3$: tris(dibenzylideneacetone) dipalladium (O)

(1) Synthesis of Partial Linker A

This compound is a compound corresponding to -E-X—NH— Where T is —NH—CO— in the linker shown by the above-described general formula (A) (-E-X-T-Y—NH—), wherein E is —CH=CH— and X is a methylene group.

(2) Synthesis of Partial Linker B

This compound is a compound corresponding to —CO—Y—NH—Where T is —NH—CO— in the linker shown by the above-described general formula (A) (-E-X-T-Y—NH—), wherein Y is a pentamethylene group.

-continued
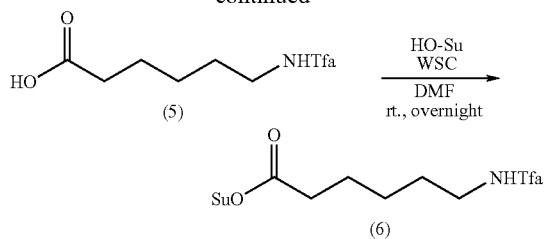
(3) Synthesis of 2'-Deoxycytidine-5'-Triphosphate Derivative [Compound Shown by General Formula (d)].
This compound is a compound corresponding to Q1-E1-X1-T1-Y1-NH— of the general formula (3') (Q1-E1-X1-T1-Y1-NH—W1), or Q2-E2-X2-T2-Y2-NH— of the general formula (4') (Q2-E2-X2-T2-Y2-NH—W2), wherein Q1 or Q2 is 2'-deoxycytidine; E1 or E2 is —CH=CH—; X1 or X2 is a methylene group; T1 or T2 is —NH—CO—; and Y1 or Y2 is a pentamethylene group.
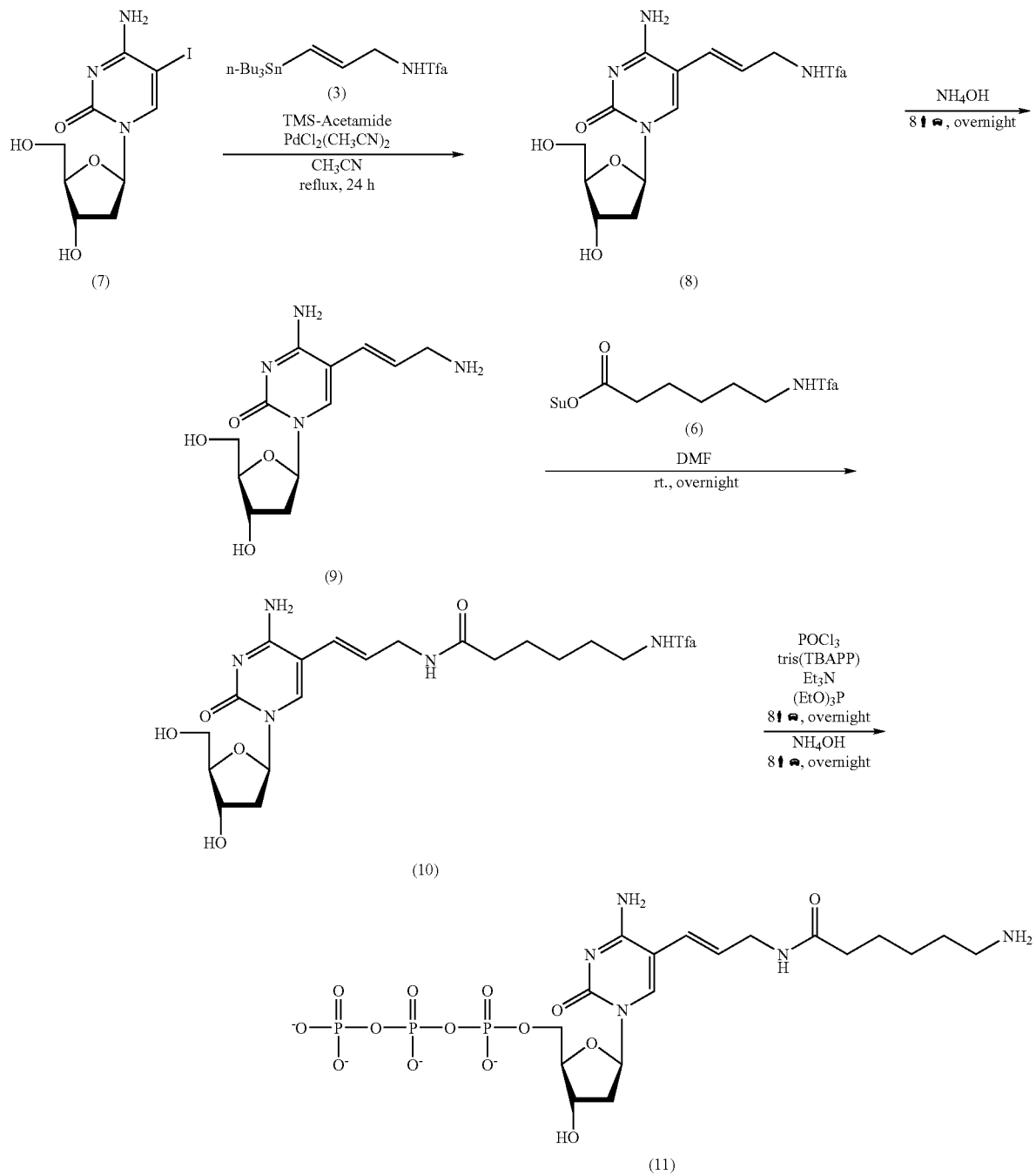

(4) Synthesis of Fluorescence Labeled 2'-Deoxycitidine-5'-Triphosphate Derivative [a Mononucleotide Labeled with the Labeling Substance (1) or (2) Involved in the Present Invention]

The aforementioned compound is a compound in which, in the general formula (3') (Q1-E1-X1-T1-Y1-NH—W1) or the general formula (4') (Q2-E2-X2-T2-Y2-NH—W2), Q1 and Q2 are 2'-deoxycytidine; E1 and E2 are —CH=CH—; X1 and X2 are a methylene group; T1 and T2 are —NH—CO—; and Y1 and Y2 are a pentamethylene group, wherein either one of W1 and W2 is the following compound (12a), and remaining one is the following compound (12b).

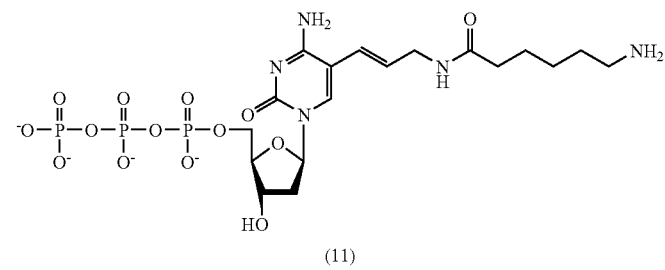

(11)

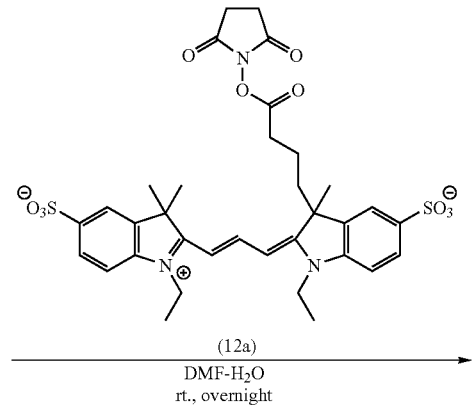

(12a)
DMF-H₂O
rt., overnight

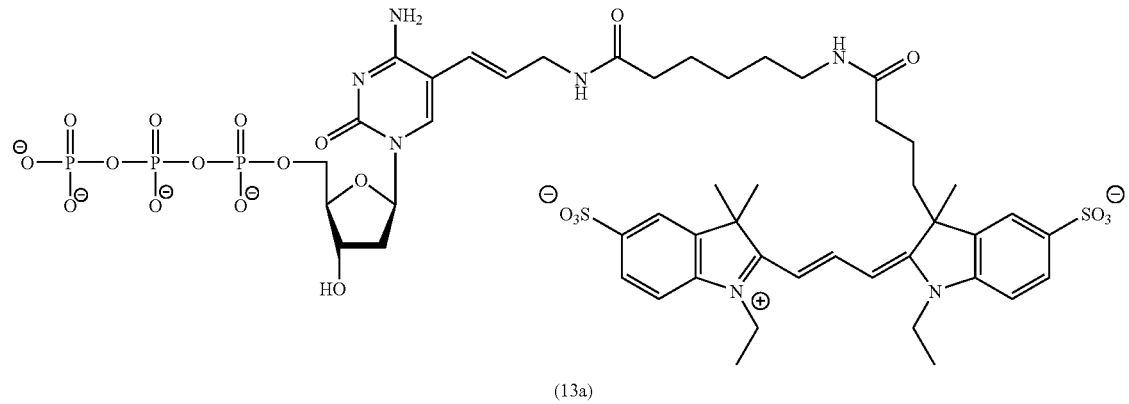

(13a)

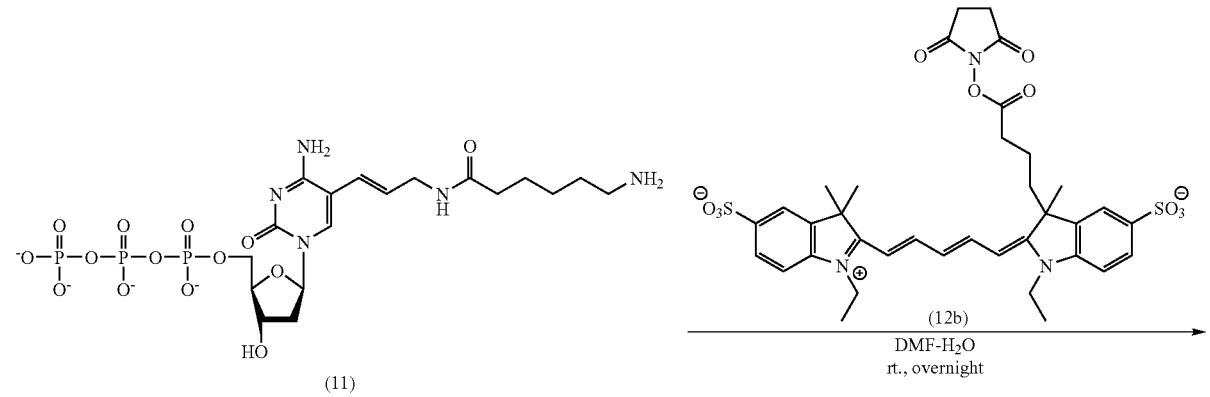

(11)

(12b)
DMF-H₂O
rt., overnight

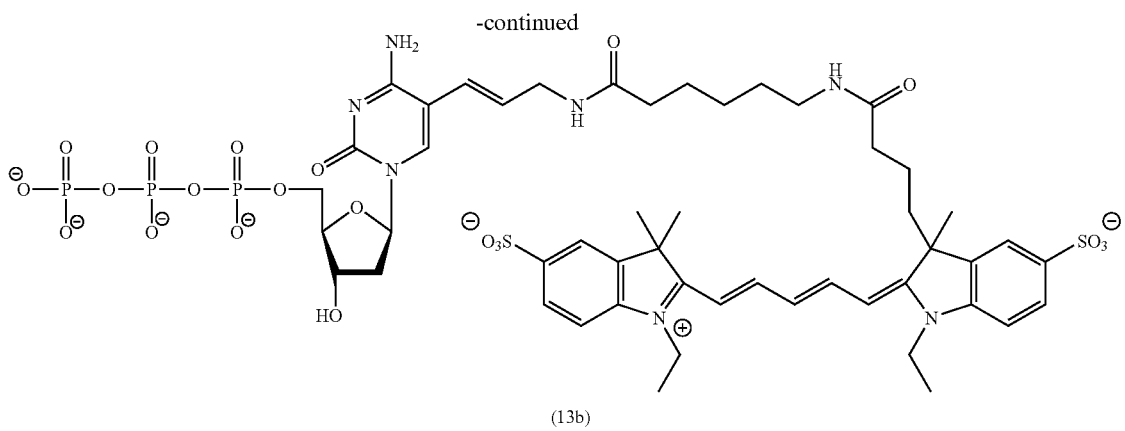
(13b)
(5) Synthesis of a 2'-deoxyuridine-5'-triphosphate derivative [compound of general formula (d)].
This compound is a compound corresponding to Q1-E1-X1-T1-Y1-NH— of the general formula (3') (Q1-E1-X1-T1-Y1-NH—W1), or Q2-E2-X2-T2-Y2-NH— of the general formula (4') (Q2-E2-X2-T2-Y2-NH—W2), wherein Q1 or Q2 is 2'-deoxyuridine; E1 or E2 is —CH=CH—; X1 or X2 is a methylene group; T1 or T2 is —NH—CO—; and Y1 or Y2 is a pentamethylene group.
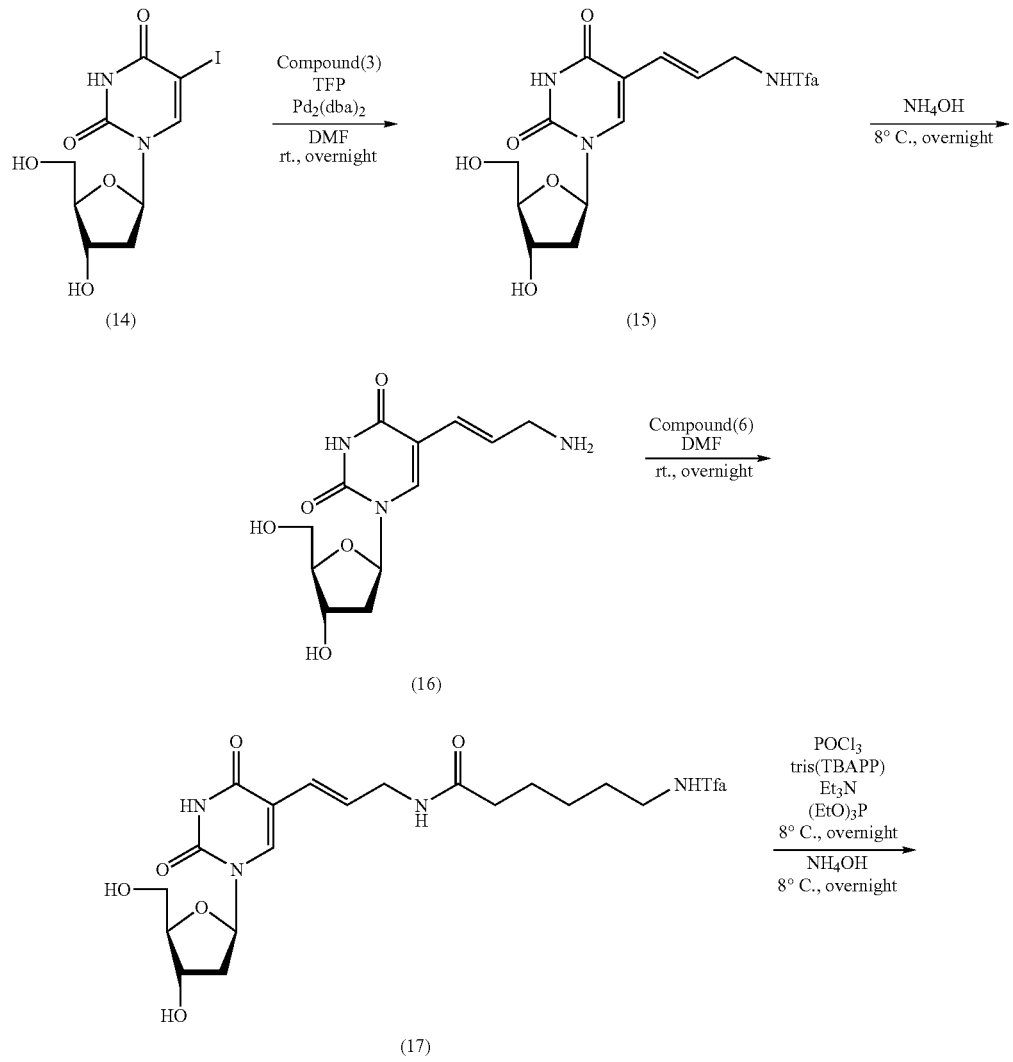

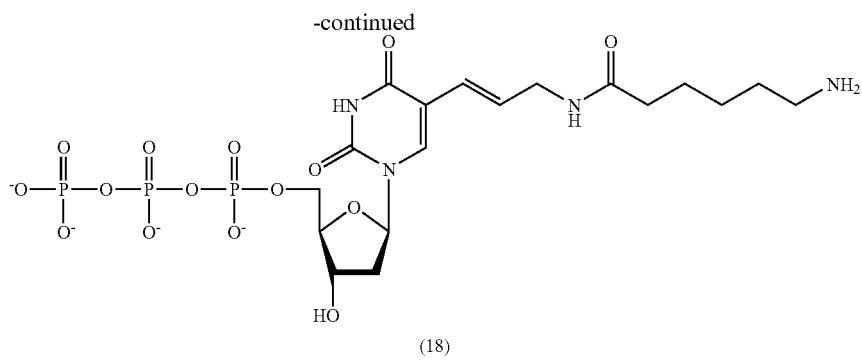

(18)

(6) Synthesis of Fluorescence Labeled 2'-Deoxyuridine-5'-Triphosphate Derivative [a Mononucleotide Labeled with the Labeling Substance (1) or (2) Involved in the Present Invention].

The aforementioned compound is a compound in which, in the general formula (3') (Q1-E1-X1-T1-Y1-NH—W1) or the general formula (4') (Q2-E2-X2-T2-Y2-NH—W2), Q1 and Q2 are 2'-deoxyuridine; E1 and E2 are —CH=CH—; X1 and X2 are a methylene group; T1 and T2 are —NH—CO—; and Y1 and Y2 are a pentamethylene group, wherein either one of W1 and W2 is the following compound (12a), and the remaining one is the following compound (12b).

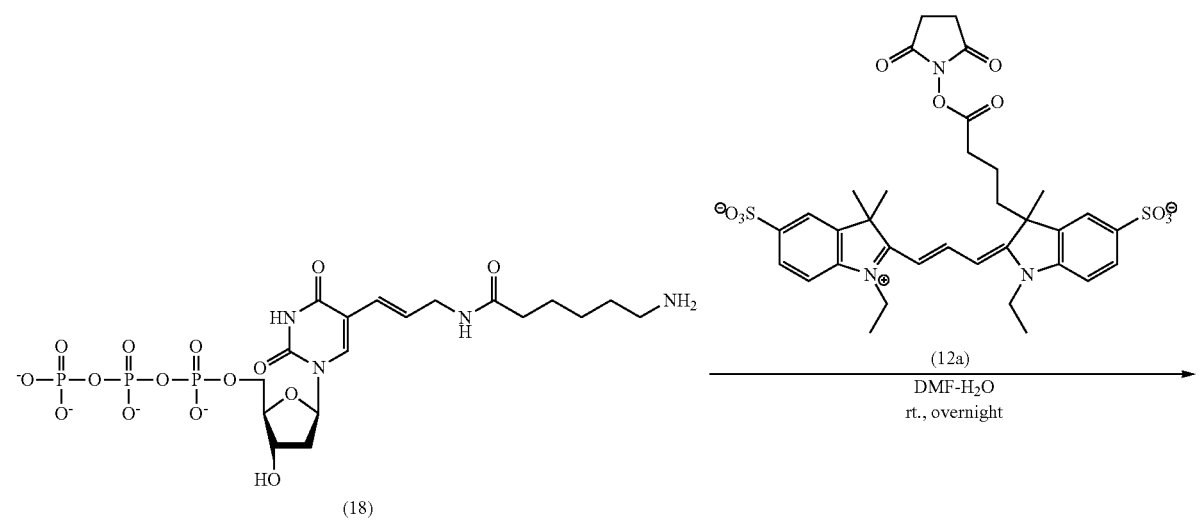

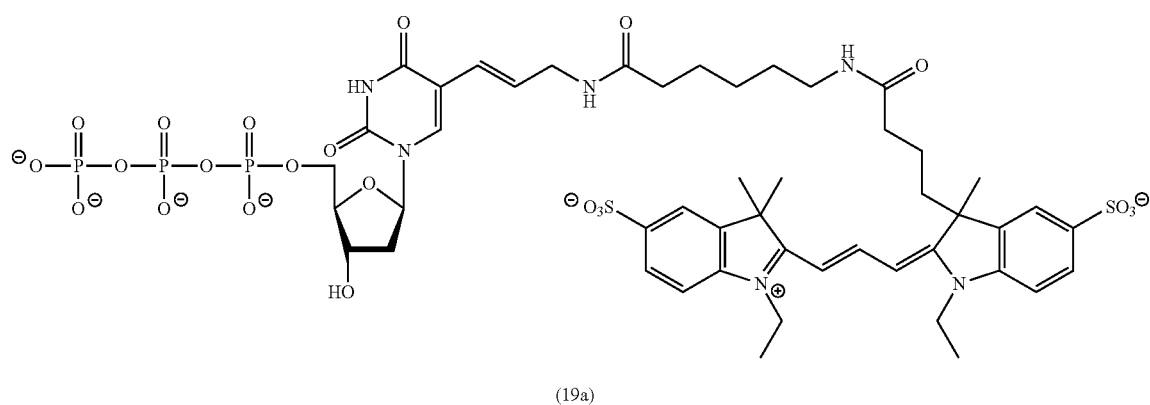

(19a)

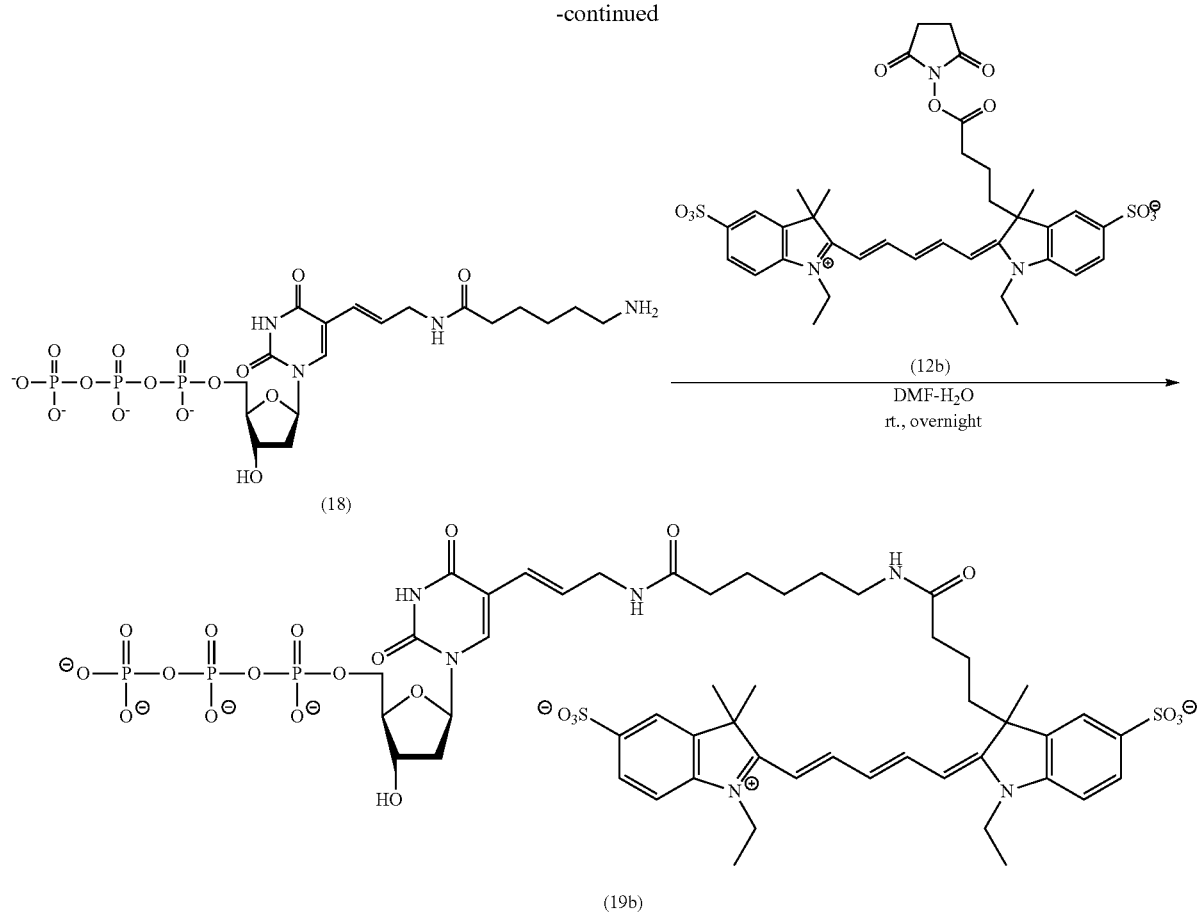

In addition, the labeled nucleotides other than those described above can also be synthesized appropriately using relevant materials according to the method described above.

When the method for labeling DNA fragment enzymatically by using a labeled mononucleotide bound with a labeling substance is utilized, all of the enzymes and reagents used in these methods described above can be used, except that the labeled mononucleotide bound with the labeling substance (1) involved in the present invention and the labeled mononucleotide bound with the labeling substance (2) involved in the present invention are used, and, for example, the followings are included.

(a) In the case of random primer method:
  i) the primer for random primer method (the primer having random nucleotide sequence), ii) at least three types of mononucleotide selected from dATP, dGTP, dCTP, and dTTP (or dUTP) other than the above-described labeled mononucleotide, preferably dATP, dGTP, dCTP, dTTP, and/or dUTP, iii) DNA polymerase (for example, Klenow Fragment, phi 29 DNA Polymerase, Bca BEST DNA Polymerase, etc.), preferably Klenow Fragment, iv) if necessary, reaction buffer solution, reaction stop solution, etc.

(b) In the case of primer method:
  i) the primer for the primer method (the primer having specific nucleotide sequence), ii) at least three types of mononucleotide selected from dATP, dGTP, dCTP, and dTTP (or dUTP) other than the above-described labeled mononucleotide, preferably dATP, dGTP, dCTP, dTTP, and/or dUTP, iii) DNA polymerase (for example, Klenow Fragment, phi 29 DNA Polymerase, Bca BEST DNA Polymerase, etc.), preferably Klenow Fragment, (iv) if necessary, reaction buffer solution, reaction stop solution, etc.

(c) In the case of nick-translation method:
  i) at least three types of mononucleotide selected from dATP, dGTP, dCTP, and dTTP (or dUTP) other than the above-described labeled mononucleotide, preferably dATP, dGTP, dCTP, dTTP, and/or dUTP, ii) DNase I and DNA Polymerase I, iii) if necessary, reaction buffer solution, reaction stop solution, etc.

(d) In the case of terminal addition reaction method (the method employing terminal deoxy transferase):
  i) terminal deoxy transferase, ii) if necessary, at least three types of mononucleotide selected from dATP, dGTP, dCTP, and dTTP (or dUTP) other than the above-described labeled mononucleotide, preferably dATP, dGTP, dCTP, dTTP, and/or dUTP, iii) further, if necessary, reaction buffer solution, etc.

(e) In the case of PCR method:
  i) the primer for PCR method (the primer having a specific nucleotide sequence), ii) at least three types of mononucleotide selected from dATP, dGTP, dCTP, and dTTP (or dUTP) other than the above-described labeled mononucleotide, preferably dATP, dGTP, dCTP, dTTP, and/or dUTP, iii) heat-resistance DNA polymerase, iv) if necessary, reaction buffer solution, etc.

(f) In the case of DOP-PCR method:
  i) the primer for the DOP-PCR method (the primer having random nucleotide sequence), ii) at least three types of mononucleotide selected from dATP, dGTP, dCTP, and dTTP (or dUTP) other than the above-described labeled mononucleotide, preferably dATP, dGTP, dCTP, dTTP, and/or dUTP, iii) heat-resistance DNA Polymerase, iv) if necessary, reaction buffer solution, etc.

In addition, when the method for labeling DNA fragment enzymatically by using a labeled oligonucleotide bound with a labeling substance as a primer is utilized, all of the enzymes and reagents used in these methods described above can be used, except that the oligonucleotide (primer) comprising the labeled nucleotide residue bound with the labeling substance (1) involved in the present invention and the oligonucleotide (primer) comprising the labeled nucleotide residue bound with the labeling substance (2) involved in the present invention are used, and, for example, the followings are included.

In this connection, as for such a primer, for example, in the case of random primer method, it is a primer having a random nucleotide sequence (the primer for the random primer method), and, in the case of the primer method, it is a primer having a specific nucleotide sequence (the primer for the primer method). In addition, in the case of the PCR method, it is a primer having a specific nucleotide sequence (the primer for the PCR method), and in the case of the DOP-PCR method, it is a primer having a random nucleotide sequence (the primer for the DOP-PCR method).

(a) In the case of random primer method:
i) dATP, dGTP, dCTP, dTTP and/or dUTP, ii) DNA polymerase (for example, Klenow Fragment, phi 29 DNA Polymerase, Bca BEST DNA Polymerase, etc.), preferably Klenow Fragment, iii) if necessary, reaction buffer solution, reaction stop solution, etc.

(b) In the case of primer method:
i) dATP, dGTP, dCTP, dTTP and/or dUTP, ii) DNA polymerase (for example, Klenow Fragment, phi 29 DNA Polymerase, Bca BEST DNA Polymerase, etc.), preferably, Klenow Fragment, iii) if necessary, reaction buffer solution, reaction stop solution, etc.

(c) In the case of PCR method:
i) dATP, dGTP, dCTP, dTTP and/or dUTP, ii) heat-resistance DNA polymerase, iii) if necessary, reaction buffer solution, etc.

(d) In the case of DOP-PCR method:
i) dATP, dGTP, dCTP, dTTP and/or dUTP, ii) heat-resistance DNA polymerase, iii) if necessary, reaction buffer solution, etc.

Furthermore, when the method for labeling DNA fragment enzymatically by using a labeled oligo- or polynucleotide bound with a labeling substance is utilized, all of the enzymes and reagents used in these methods described above can be used, except that the oligo- or polynucleotide comprising the labeled nucleotide residue bound with the labeling substance (1) involved in the present invention and the oligo- or polynucleotide comprising the labeled nucleotide residue bound with the labeling substance (2) involved in the present invention are used, and, for example, the followings are included.

(a) In the case of ligation method
i) ligase, ii) ATP, iii) if necessary, reaction buffer solution, etc.

It should be noted that, after labeling the test genomic DNA fragment and the control genomic DNA fragment by the method as described above, it is preferable to remove the free labeling substance (or the free labeled mononucleotide) by a purification method well known per se (for example, by the ethanol precipitation method, etc.). In addition, on the occasion of using the obtained labeled test genomic DNA fragment and the labeled control genomic DNA fragment in the hybridization process to be described hereinafter, it is preferable to treat them previously with Cot-1 DNA and the like to block nonspecific repeated sequences present in these genomic DNA fragments. In this connection, when the obtained labeled test genomic DNA fragment and the labeled control genomic DNA fragment are double-stranded DNA, it is common to apply them to the hybridization process after making them single strand by heat-treatment etc.

(4) Sample Nucleic Acid

In the present invention, "sample nucleic acid" is the one which comprises a nucleotide sequence to detect the difference between the test genomic DNA fragment and the control genomic DNA fragment as mentioned above (namely, abnormality in the copy number of the test genomic DNA).

That is, the "sample nucleic acid" may be the one which comprises a nucleotide sequence corresponding to a whole genome (the genome substantially corresponding to the whole chromosome) of cell (living organism) to be inspected (to be detected and investigated for copy number abnormality or chromosomal aberration), or the one which comprises a nucleotide sequence corresponding to a specific genome [the genome corresponding to a specific chromosome, a specific region (a specific site) of chromosome or a specific gene].

Such a "sample nucleic acid" includes, for example, whole chromosome, specific chromosome, specific region thereof, genomic DNA fragment (for example, the one having a DNA sequence substantially corresponding to the whole chromosome, etc.), a part of genomic DNA fragment (for example, the one having a DNA sequence substantially corresponding to a specific chromosome or a specific region of the chromosome, the one having a DNA sequence corresponding to a specific gene, etc.), mRNA (the entire or a part), cDNA (the entire or a part, amplification products thereof), and the like.

Specifically, for the chromosome (all chromosomes, specific chromosomes, specific region thereof), the meta-phase (metaphase chromosome) of normal lymphocyte or a part of it is usually used, but is not limited thereto.

In addition, for the genomic DNA fragment, the genomic DNA fragment extracted from cell or a cell population by the method well known per se, cloned genomic DNA fragment, a part of these genomic DNA fragments are included, and the synthetic oligo-DNA fragments having a sequence of the specific region in these genomic DNA fragment, the DNA fragments which were fragmented by restriction enzymes or by chemical fragmentation, the amplification products thereof can also be used.

In the above description, the cloned genomic DNA fragment means the genomic DNA fragment which has been cloned into an appropriate vector, and includes, for example, the genomic DNA fragment which has been cloned into an artificial chromosome, such as BAC (Bacterial Artificial Chromosome), YAC (Yeast Artificial Chromosome), PAC (P1-derived Artificial chromosome), HAC (Human Artificial Chromosome), MAC (Mammalian Artificial Chromosome), TAC (Transformation competent Artificial Chromosome), and, for example, the genomic DNA fragment which has been cloned into the plasmid vector, the cosmid vector, the virus vector, etc. are included.

Such sample nucleic acid can be prepared by extraction method well known per se or using a commercial extraction kit. In addition, it is also possible to employ a commercial product.

(5) Array CGH

The present invention is effective in so-called array CGH method using a substrate to which the above-described sample nucleic acid is immobilized (fixed).

The array CGH method is a method for performing the CGH method (analysis) using a substrate (for example, a slide glass, a placoid tip of glass, metal or resin, micro beads, fibrous carrier, etc.) to which the above-described sample nucleic acid has been immobilized (fixed) covalently or non-covalently.

Among them, the present invention is effective when a substrate to which the above-described genomic DNA fragment, a part of the genomic DNA fragment, cDNA, etc. has been immobilized (fixed) is employed, and in particular, the present invention is effective when a substrate to which the cloned genomic DNA fragment has been immobilized (fixed) is employed.

In addition, as for the substrate to which the cloned genomic DNA fragment has been immobilized (fixed), it is preferable to use a substrate to which the genomic DNA fragment which has been cloned into BAC (BAC array) has been immobilized (fixed).

It should be noted that, the substrate to which the cloned genomic DNA fragment has been immobilized (fixed) may be the one which comprises the sufficient number of the genomic DNA fragment corresponding to the whole cell (living organism) to be used as a test subject (to be detected and investigated for copy number abnormality or chromosomal aberration), or the one which comprises the genomic DNA fragment corresponding to the specific region (specific site) of the chromosome or the objective gene to detect the difference as described above (abnormality in copy number). Namely, it may be the one to which plural number of DNA fragments have been immobilized (fixed) in such way that these plural number of DNA fragments are combined and cover in an integrated manner the DNA sequence corresponding to substantially all of the chromosome (or specific chromosome) or a specific region of the chromosome, or the one to which a nucleic acid fragment (DNA fragment, RNA fragment) having one type or two or more types of DNA sequence corresponding to one type or two or more types of the specific gene (or mRNA, cDNA, etc.) has been immobilized (fixed).

In addition, as for these cloned genomic DNA fragments, it is preferable that the position of the fragment in the chromosome has been identified (mapped).

The substrate to which the sample nucleic acid has been immobilized (fixed) can be prepared by the method well known per se (for example, the method described in JP-A-2006-115844, JP-A-2005-304481, JP-A-2006-94726, JP-A-2005-00023, JP-A-2005-525786, JP-A-2005-304497, etc.) and the like.

In addition, it is also possible to employ commercial products (for example, "MacArray" produced by Macrogen, "SpectralChip" produced by U.S. Spectral Genomics, "GeneChip" produced by Affymetrix, "CodeLink" produced by GE Healthcare, "AceGene" produced by DNA Chip Research Institute and so on).

(6) Concrete Method

The method of the present invention can be practiced according to the CGH method based on the above-described principle.

That is, (a) the above-described sample nucleic acid is hybridized competitively with (b) the labeled test genomic DNA fragment which has been labeled with either one of the labeling substance (1) or the labeling substance (2) involved in the present invention and the labeled control genomic DNA fragment which has been labeled with the other labeling substance (hybridization process), and amplification or deletion in the test genomic DNA (namely, abnormality in copy number of the test genomic DNA) is detected using the obtained fluorescence intensity as an indicator (analysis process).

In the above description, the hybridization process is a process in which the labeled test genomic DNA fragment and the labeled control genomic DNA fragment are hybridized competitively with the sample nucleic acid, and the process may be carried out, for example, by using a mixed solution containing the labeled test genomic DNA fragment and the labeled control genomic DNA fragment, and contacting these labeled test genomic DNA fragment and the labeled control genomic DNA fragment simultaneously with the sample nucleic acid.

The total amount of the labeled test genomic DNA fragment and the labeled control genomic DNA fragment used herein is usually 0.001-1000 µg, preferably 0.01-100 µg, more preferably 1-32 µg.

In addition, as for a ratio of the labeled test genomic DNA fragment and the labeled control genomic DNA fragment to be used, a weight of the control genomic DNA per one weight of the test genomic DNA is, as a weight ratio in the mixed solution, usually 0.01 times to 100 times, preferably 0.1 times to 10 times, more preferably 0.5 time to 2 times.

The temperature of hybridization is usually 0° C.-95° C., preferably 30° C.-70° C., more preferably 35° C.-46° C., and the time of a hybridization is usually for 1 hour to 480 hours, preferably for 4 hours to 240 hours, more preferably for 24 hours to 120 hours, still more preferably for 36 hours to 72 hours.

In addition, on the occasion of hybridization, in order to block nonspecific repeated sequence which may exist in the genomic DNA fragment, it is preferable to carry out hybridization under the existence of blocking agent such as Cot-1 DNA and the like (for example, under the co-existence of blocking agent such as Cot-1 DNA and the like in the above-described mixed solution). In addition, in order to prevent non-specific binding of the labeled test genomic DNA fragment and the labeled control genomic DNA fragment to the substrate, it can also be carried out under the presence of salmon sperm DNA.

It should be noted that, in order to eliminate non-specific signal as much as possible, it is preferable to rinse the obtained sample nucleic acid with an appropriate cleaning solution after hybridization.

The above-described hybridization process is preferably carried out under "stringent condition". The "stringent condition" may be set appropriately by selecting from the conditions employed in the CGH method well known per se, and not particularly limited, and specifically, for example, the stringent condition is such one where "the hybridization is carried out in a hybridization buffer (pH 7) containing 50% formamide, 2×SSC and 4% SDS, and 10% dextran sulfate, or in a hybridization buffer which provides a stringent condition equivalent to this buffer for 36 hours-72 hours at 35-42° C.; after pre-washing, if necessary, with 2×SSC (pH 7) containing 50% formamide, 2×SSC (pH 7) containing 0.1% SDS and 0.1 M phosphate buffer (pH 8) containing 0.1% NP-40 or with a buffer solution which provides a stringent condition equivalent to these buffers, washing with 2×SSC or a solution with an equivalent salt concentration and the like". It should be noted that, it goes without saying that the different hybridization and washing conditions which provide similar stringency conditions can be utilized.

In the above description, the analysis process is a process where after carrying out the hybridization process, the fluorescence intensity on the sample nucleic acid is measured, and amplification or deficiency in the test genomic DNA (namely, abnormality in copy number of the test genomic DNA) is detected using fluorescence intensity obtained as an indicator.

The fluorescence intensity on the sample nucleic acid can be determined by obtaining fluorescence image on the sample nucleic acid using an image analyzer such as, for example, laser scanner and CCD camera, etc., and by analyzing the acquired fluorescence image using an image analysis software etc.

In addition, in order to detect the amplification or deficiency in the test genomic DNA (namely, abnormality in copy number of the test genomic DNA) using the fluorescence intensity obtained as an indicator, for example, the fluorescence intensity ratio of the labeling substance derived from the test genomic DNA fragment to the labeling substance derived from the control genomic DNA fragment is determined from the fluorescence intensity obtained, using an image analysis software etc., and analysis of the ratio may be carried out.

That is, when the ratio of fluorescence intensity of the labeling substance derived from the test genomic DNA fragment to the labeling substance derived from the control genomic DNA fragment is high, this indicates that the aforementioned part (region) in the sample nucleic acid has been hybridized more strongly with the test genomic DNA fragment as compared with the control genomic DNA fragment, and amplification (increase in the copy number) of a region corresponding to aforementioned part (region) in the sample nucleic acid is detected in the test genomic DNA. On the contrary, when the ratio of fluorescence intensity of the labeling substance derived from the test genomic DNA fragment to the fluorescence intensity of the labeling substance derived from the control genomic DNA fragment is low (or else, when the fluorescence of the labeling substance derived from the test genomic DNA fragment is not detected), this indicates that the aforementioned part (region) in the sample nucleic acid has hybridized more strongly with the control genomic DNA fragment as compared with the test genomic DNA fragment (or else, only the control genomic DNA fragment has been hybridized), and deletion of the region corresponding to the aforementioned part (region) in the sample nucleic acid (the copy number has been decreased, or else not copied) is detected in the test genomic DNA. It should be noted that, on the occasion of determining the ratio of fluorescence intensity in the above description, it is preferable to correct an average value of the fluorescence intensity of the labeling substances derived from the test genomic DNA fragment and an average value of the fluorescence intensity of the labeling substances derived from the control genomic DNA fragment [in other words, an average value of the fluorescence intensity of the labeling substance (1) involved in the present invention and an average value of the fluorescence intensity of the labeling substance (2) involved in the present invention] so that both values become identical, and then determine the ratio of the fluorescence intensity based on the aforementioned corrected values.

In addition, in the present invention, the process of judgment on the copy number abnormality (or chromosomal aberration) in the above-described test genomic DNA [in other words, the process of quantitative (or semi-quantitative) determination on the presence of the copy number abnormality (or the presence of chromosomal aberration) in the test genomic DNA, or on the increased amount or decreased amount of the copy number] and the process of preparation of the above-described labeled test genomic DNA fragment and the labeled control genomic DNA fragment may be included.

Although the method of the present invention is as described above, specifically, it can be practiced according to the method described, for example, in WO93/018186 (JP-A-07-505053), JP-A-2006-115844, JP-A-2005-304481, JP-A-2006-94726, JP-A-2005-500023, JP-A-2005-525786, JP-A-2005-304497, JP-A-11-258233, and so on, and all of the reagents and conditions (for example, the hybridization condition, etc.) described therein can be used.

Hereinafter, the case where a BAC array is employed will be described more specifically as an example of the method of the present invention.

(a) Preparation of Labeled Test Genomic DNA Fragment and Labeled Control Genomic DNA Fragment For example, the labeled test genomic DNA fragment which is labeled with the labeling substance (1) involved in the present invention [or the labeling substance (2) involved in the present invention] and the labeled control genomic DNA fragment which is labeled with the labeling substance (2) involved in the present invention [or the labeling substance (1) involved in the present invention] are synthesized, respectively, through the use of random primer method, and using the test genomic DNA fragment and the control genomic DNA fragment as a template, each of which are extracted from cell or cell population by the method as mentioned above. Thereby, the labeled test genomic DNA fragment and the labeled control genomic DNA fragment having about 100 to 5000 by of chain length can be obtained. In addition, if necessary, the labeled genomic DNA fragment is purified to remove the labeling substance which is not taken into the labeled genomic DNA fragment from a solution containing the labeled test genomic DNA fragment or the labeled control genomic DNA fragment by a method well known per se or using a commercially available purification kit.

To the solution containing the labeled test genomic DNA fragment and labeled control genomic DNA fragment which are obtained, Cot-1 DNA (50-100 μg) and the like is added to block the repeated sequence, and these are precipitated by ethanol precipitation method and the like, and then a precipitated mixture of purified labeled test genomic DNA fragment, the labeled control genomic DNA fragment and Cot-1 DNA is dissolved in a hybridization solution [for example, 50% formamide/2×SSC (2×SSC: double concentration of standard citrate buffer)/10% dextran sulfate/4% SDS (SDS: sodium dodecyl sulfate)/100 mg/ml yeast tRNA, and pH 7.0]. The hybridization solution in which the labeled test genomic DNA fragment and the labeled control genomic DNA fragment have been dissolved is subjected, for example, to heat treatment at 70° C. for 10 minutes to make the labeled test genomic DNA fragment and the labeled control genomic DNA fragment single-stranded form, and after that, the non-specific repeated sequence which may exist in the labeled test genomic DNA fragment and the labeled control genomic DNA fragment is blocked with Cot-1 DNA by incubating at 37° C. for 60 minutes.

(b) Pretreatment of BAC Array

For example, as for the BAC array obtained as described above or the commercially available BAC array, when the sample nucleic acid (DNA) immobilized (fixed) on the array is single strand, it can be applied to hybridization as it is; and if the aforementioned sample nucleic acid (DNA) is in the state of double strand, the double-stranded sample nucleic acid (DNA) is converted to single strand configuration by heating about 1 minute in a boiling water etc., and dried, then applied to the hybridization.

In addition, to inhibit adsorption of the labeled test genomic DNA fragment and the labeled control genomic DNA fragment to array vehicle, the array vehicle is better to be immersed in the hybridization solution containing salmon sperm DNA (10 mg/ml) for about 30 minutes, then rinsed with purified water and dried up immediately in advance.

(c) Hybridization

The sample nucleic acid (DNA) fragment (BAC clone DNA fragment) immobilized (fixed) on the BAC array is contacted with the obtained labeled test genomic DNA fragment and the labeled control genomic DNA fragment, the competitive hybridization reaction of the sample nucleic acid (DNA) with the labeled test genomic DNA fragment and the labeled control genomic DNA fragment is carried out under the condition as described above. In addition, the contact of the sample nucleic acid on a BAC array with the labeled test genomic DNA fragment and the labeled control genomic DNA fragment is carried out by dropping the hybridization solution obtained by the method as described above in which the labeled test genomic DNA fragment and the labeled control genomic DNA fragment are dissolved on a BAC array, and after dropping, hybridization is carried out under humidified condition by covering an array with a cover glass etc. In addition, the contact/hybridization may be carried out using a commercially available device for hybridization on array.

After the hybridization reaction is completed, the obtained BAC array is washed to keep specific binding of the sample nucleic acid (DNA) with the labeled test genomic DNA fragment and the labeled control genomic DNA fragment, and remove nonspecific hybridization or adsorbed labeled test genomic DNA fragment and labeled control genomic DNA fragment from the sample nucleic acid (DNA). Washing of the BAC array is carried out, for example, by immersing the array in a 50% formamide/2×SSC, pH 7, warmed at 46° C., for 15 minutes; then in a 0.1% SDS/2×SSC, pH 7 for 30 minutes; followed by immersing in a 0.1% NP40/0.1 M phosphate buffer, pH 7 of room temperature for 15 minutes; and 2×SSC, pH 7 for 5 minutes; and after washing is completed, the obtained BAC array is better to rinse with ethanol and dried.

(d) Measurement of Fluorescence Intensity

Measurement is carried out for the fluorescence intensity (signal) derived from the test genomic DNA fragment and the fluorescence intensity (signal) derived from the control genomic DNA fragment each of which have been hybridized with the sample nucleic acid (DNA) immobilized (fixed) on a BAC array. Fluorescence intensity is determined, for example, by obtaining the fluorescence images of each sample nucleic acid (DNA) with an image analyzer such as laser scanner and CCD camera, and by analyzing the acquired fluorescence images using an image analysis software etc.

(e) Detection of Amplification or Deletion

The detection of amplification or deletion in the test genomic DNA (namely, abnormality in copy number of the test genomic DNA) is performed, for example, by obtaining the fluorescence intensity ratio of the labeling substance derived from the test genomic DNA fragment and the labeling substance derived from the control genomic DNA fragment from the fluorescence intensity obtained using an image analysis software etc., and analyzing it.

Namely, in the genomic region corresponding to the sample nucleic acid (DNA) fragment (BAC clone DNA fragment), if copy number increase (amplification) has arisen in the original cell (for example, abnormal cell and the like) from which the test genomic DNA fragment was extracted, the test genomic DNA fragment would hybridize in a relatively larger amount as compared with the control genomic DNA fragment. On the other hand, if copy number decrease (deletion) has arisen in the original cell (for example, abnormal cell and the like) from which the test genomic DNA fragment was extracted, the control genomic DNA fragment would hybridize in a relatively larger amount as compared with the test genomic DNA fragment. Therefore, by comparing the fluorescence intensity (signal) derived from the test genomic DNA fragment with the fluorescence intensity (signal) derived from the control genomic DNA fragment for every sample nucleic acid (DNA fragment) on the BAC array (namely, by calculating these fluorescence intensity ratios, and analyzing them), judgment can be made whether copy number increase has arisen; whether copy number decrease has arisen; or whether copy number is in the normal level in the original cells (for example, abnormal cell and the like) from which the test genomic DNA fragment was extracted.

(7) Kit of the Present Invention

The kit of the present invention is intended to be used for practicing the above-described method of the present invention.

Such kit is (i) the one which comprises at least a nucleotide residue labeled with the labeling substance (1) of the present invention and a nucleotide residue labeled with the labeling substance (2) of the present invention, which are used for labeling the test genomic DNA fragment and the control genomic DNA fragment, preferably, the above-described labeled nucleotide residue shown by the general formula (3) and the labeled nucleotide residue shown by the general formula (4), more preferably, labeled nucleotide residue shown by the general formula (3') and the labeled nucleotide residue shown by the general formula (4'), and preferably (ii) the one which further comprises at least one kind selected from the above-described primers, enzymes, reagents and so on.

Such kit includes, for example, those which comprise the following constituent elements.

It should be noted that, the preferable embodiments and specific examples of constituent elements are as mentioned above.

(a) In the Case of a Kit for the Random Primer Method Using a Labeled Mononucleotide:

i) the mononucleotide labeled with the labeling substances (1) of the present invention and the mononucleotide labeled with the labeling substances (2) involved in the present invention; ii) the primer for the random primer method (the primer having random nucleotide sequences); iii) at least three types of mononucleotides selected from dATP, dGTP, dCTP, and dTTP (or dUTP) other than the above-described labeled mononucleotide, preferably dATP, dGTP, dCTP, dTTP, and/or dUTP; iv) DNA polymerase (for example, Klenow Fragment, phi 29 DNA polymerase, Bca BEST DNA polymerase, etc.), preferably Klenow Fragment; v) if necessary, reaction buffer solution, reaction stop solution, etc.

(b) In the Case of the Kit for the Primer Method Employing a Labeled Mononucleotide:

i) the mononucleotide labeled with the labeling substances (1) of the present invention and the mononucleotide labeled with the labeling substances (2) involved in the present invention; ii) the primer for the primer method (primer having specific sequence); iii) at least three types of mononucleotide selected from dATP, dGTP, dCTP, and dTTP (or dUTP) other than the above-described labeled mononucleotide, preferably dATP, dGTP, dCTP, dTTP, and/or dUTP; iv) DNA polymerase (for example, Klenow Fragment, phi 29 DNA polymerase, Bca BEST DNA polymerase, etc.), preferably Klenow Fragment; v) if necessary, reaction buffer solution, reaction stop solution, etc.

(c) In the Case of the Kit for Nick-Translation Method Employing a Labeled Mononucleotide:

i) the mononucleotide labeled with the labeling substances (1) of the present invention and the mononucleotide labeled with the labeling substances (2) involved in the present invention; ii) at least three types of mononucleotides selected from dATP, dGTP, dCTP, and dTTP (or dUTP) other than the above-described labeled mononucleotides, preferably dATP, dGTP, dCTP, dTTP, and/or dUTP; iii) DNase I and DNA polymerase I; iv) if necessary, reaction buffer solution, reaction stop solution, etc.

(d) In the Case of the Terminal Addition Reaction Method (a Method Employing Terminal Deoxytransferase) Employing a Labeled Mononucleotide:
i) the mononucleotide labeled with the labeling substances (1) of the present invention and the mononucleotide labeled with the labeling substances (2) involved in the present invention; ii) terminal deoxytransferases; iii) if necessary, at least three types of mononucleotides selected from dATP, dGTP, dCTP, and dTTP (or dUTP) other than the above-described labeled mononucleotides, preferably dATP, dGTP, dCTP, dTTP, and/or dUTP; iv) further, if necessary, reaction buffer solution, etc.

(e) In the Case of the PCR Method Employing a Labeled Mononucleotide:
i) the mononucleotide labeled with the labeling substances (1) of the present invention and the mononucleotide labeled with the labeling substances (2) involved in the present invention; ii) the primer for PCR method (primer with a specific nucleotide sequence); iii) at least three types of mononucleotides selected from dATP, dGTP, dCTP, and dTTP (or dUTP) other than the above-described labeled mononucleotides, preferably dATP, dGTP, dCTP, dTTP, and/or dUTP; iv) heat resistant DNA polymerase; v) if necessary, reaction buffer solution etc.

(f) In the Case of the DOP-PCR Method Employing a Label Mononucleotide:
i) the mononucleotide labeled with the labeling substances (1) of the present invention and the mononucleotide labeled with the labeling substances (2) involved in the present invention; ii) the primer for DOP-PCR method (primer with a random nucleotide sequence); iii) at least three types of mononucleotides selected from dATP, dGTP, dCTP, and dTTP (or dUTP) other than the above-described labeled mononucleotides, preferably dATP, dGTP, dCTP, dTTP, and/or dUTP; iv) heat resistant DNA polymerase; v) if necessary, reaction buffer solution etc.

(g) In the Case of the Random Primer Method Employing Labeled Oligonucleotide as the Primer:
i) the oligonucleotide (the primer with a random nucleotide sequence for the random primer method) comprising the labeled nucleotide residue bound with the labeling substance (1) involved in the present invention and the oligonucleotide (the primer with a random nucleotide sequence for the random primer method) comprising the labeled nucleotide residue bound with the labeling substance (2) involved in the present invention; ii) dATP, dGTP, dCTP, dTTP, and/or dUTP; iii) DNA polymerase (for example, Klenow Fragment, phi 29 DNA polymerase, Bca BEST DNA polymerase, etc.), preferably Klenow Fragment; iv) if necessary, reaction buffer solution, reaction stop solution, etc.

(h) In the Case of the Primer Method Employing a Labeled Oligonucleotide as the Primer:
i) the oligonucleotide (the primer with a specific nucleotide sequence for the primer method) comprising the labeled nucleotide residue bound with the labeling substance (1) involved in the present invention and the oligonucleotide (the primer with a specific nucleotide sequence for the primer method) comprising the labeled nucleotide residue bound with the labeling substance (2) involved in the present invention; ii) dATP, dGTP, dCTP, dTTP, and/or dUTP; iii) DNA polymerase (for example, Klenow Fragment, phi 29 DNA polymerase, Bca BEST DNA polymerase, etc.), preferably Klenow Fragment; iv) if necessary, reaction buffer solution, reaction stop solution, etc.

(i) In the Case of the PCR Method Employing a Labeled Oligonucleotide as the Primer:
i) the oligonucleotide (the primer with a specific nucleotide sequence for the PCR method) comprising the labeled nucleotide residue bound with the labeling substance (1) involved in the present invention and the oligonucleotide (the primer with a specific nucleotide sequence for the PCR method) comprising the labeled nucleotide residue bound with the labeling substance (2) involved in the present invention; ii) dATP, dGTP, dCTP, dTTP, and/or dUTP; iii) heat resistant DNA polymerase; iv) if necessary, reaction buffer solution, etc.

(j) In the Case of the DOP-PCR Method Employing a Labeled Oligonucleotide as the Primer:
i) the oligonucleotide (the primer with a random nucleotide sequence for the DOP-PCR method) comprising the labeled nucleotide residue bound with the labeling substance (1) involved in the present invention and the oligonucleotide (the primer with a random nucleotide sequence for the DOP-PCR method) comprising the labeled nucleotide residue bound with the labeling substance (2) involved in the present invention; ii) dATP, dGTP, dCTP, dTTP, and/or dUTP; iii) heat resistant DNA polymerase; iv) if necessary, reaction buffer solution etc.

(k) In the Case of the Kit for the Ligation Method:
i) the oligo- or polynucleotide comprising the labeled nucleotide residue bound with the labeling substance (1) involved in the present invention and the oligo- or polynucleotide comprising the labeled nucleotide residue bound with the labeling substance (2) involved in the present invention; ii) ligase; iii) ATP; iv) if necessary, reaction buffer solution, reaction stop solution, etc.

Further, by adding enzymes and reagents other than those described above, it can also make a kit of the present invention. Such reagents include, for example, at least one kind selected from the following a)-k), but not limited thereto.

a) Reaction buffer solution for the enzymes for use in labeling the DNA fragment (for example, Good's buffer solution containing salts such as magnesium salt, mercaptoethanol or dithiothreitol, etc.);

b) The reaction stop solution for use in stopping the reaction of the enzyme for labeling the DNA fragment (for example, water and Good's buffer solution containing reaction stop agent such as chelating agent);

c) The reagents for use in purifying the labeled mononucleotide and the labeled genomic DNA fragment (the test genomic DNA fragment, the control genomic DNA fragment);

d) Sample nucleic acid and a substrate for use in immobilizing (fixing) sample nucleic acid, or a substrate immobilized (fixed) with sample nucleic acid;

e) Buffer solution for hybridization [for example, a buffer solution (pH 7) comprising 50% formamide, 2×SSC, 4% SDS and 10% dextran sulfates, etc.];

f) Reagents for prevention of non-specific adsorption at the time of hybridization (for example, salmon sperm DNA, t-RNA, Cot-1 DNA, etc.);

g) Washing liquid after hybridization (for example, 2×SSC containing 50% formamide, 2×SSC containing 0.1% SDS, 0.1M phosphate buffer containing 0.1% NP-40, 2×SSC, Ethanol, isopropanol, etc.);

h) Extraction reagents for extracting test genomic DNA fragment and/or control genomic DNA fragment (for example, buffer solution for homogenation, RNase for DNA purification, proteases for protein removal, phenol, chloroform, SDS, β-mercaptoethanol, column for purification, etc.);

i) Fragmentation reagents for fragmenting the test genomic DNA fragment and/or the control genomic DNA fragment (for example, restriction enzymes etc.);

j) Reagents for electrophoresis for confirmation of the test genomic DNA fragment and/or the control genomic DNA fragment which were obtained, for example, after performing extraction, labeling, fragmentation, purification, etc. (agarose or polyacrylamide gel, loading buffer solution, the reagent for ethidium bromide staining, etc.);

k) Reagents for alcohol precipitation (for example, ethanol solution, isopropanol solution, polymer career, sodium acetate solution, etc.), and so on.

In addition, the kit may contain an instruction manual and the like for practicing the method of the above-described present invention. The aforementioned "instruction manual" means the instruction for use the kit, a package insert, or a pamphlet (leaflet) in which the feature, the principle, the operating procedure, etc. in the method of the present invention are substantially indicated by text or chart and the like.

Hereinafter, the present invention will be further explained in detail by referring to the following Synthesis Examples and Examples, but the scope of the present invention should not be limited thereto.

EXAMPLE

Synthesis Example 1

Synthesis of Labeled Mononucleotides (fluorescence labeled 2'-deoxycytidine-5'-triphosphate derivatives)

The mononucleotide (2'-deoxycytidine-5'-triphosphate) which was labeled with the labeling substance (1) involved in the present invention and the mononucleotide (2'-deoxycytidine-5'-triphosphate) which was labeled with the labeling substance (2) involved in the present invention were synthesized as follows according to the synthesis routes as described above, respectively.

(1) Synthesis of Partial Linker A
(i) Trifluoroacetylation (Tfa) (the 1st Step)

After methyl-trifluoroacetate (MeOTfa) (54 g) was added dropwise to Propargylamine [compound (I) in the above-described synthesis route] (produced by Tokyo Chemical Industry Co. Ltd.) (21 g) under ice-cooling, the mixture was stirred at room temperature for 2 hours. After completion of the reaction, the reaction mixture was subjected to purification by distillation under reduced pressure (20 mmHg, 74° C.), and a compound [compound of (2) in the above-described synthesis route] (56 g) was obtained (yield; 98.1%).

(ii) Tri(n-butyl)tin ($Bu_3Sn$)-Modification (the 2nd Step)

Compound (2) [compound (2) in the above-described synthesis route] (15 g) was dissolved in benzene (300 mL), and after addition of tri(n-butyl)tin hydride ($Bu_3SnH$) (35 mL) and azoisobutyronitrile (AIBN) (2.1 g), the reaction mixture was stirred under reflux for 1.5 hours. After completion of the reaction, the reaction mixture was concentrated under reduced pressure. Residue was purified through a silica gel column (eluent; AcOEt:Hexane=1:20), and compound (3) (partial linker A) [compound (3) in the above-described synthetic pathway]) (11.4 g) was obtained (yield; 25.8%).

(2) Synthesis of Partial Linker B
(i) Trifluoroacetylation (Tfa) (the 3rd Step)

6-Aminohexanoic acid [compound (4) in the above-described synthesis route] (produced by Wako Pure Chemical Industries) (10 g) was suspended in $CHCl_3$, and after addition of methyl trifluoroacetate (MeOTfa) (25 g) and triethylamine ($Et_3N$) (25 mL), the mixture was stirred at room temperature for two days. After completion of the reaction, solvent was distilled away, and the compound [compound (5) in the above-described synthesis route] (8.4 g) was obtained by crystallization from water (yield; 48.6%).

(ii) Active Esterification (the 4th Step)

Compound (5) [compound (5) in the above-described synthesis route] (2.3 g) was dissolved in N,N-dimethylformamide (DMF) (50 mL), and N-hydroxy succinimide (HO-Su) (1.4 g) and WSC (2.3 g) were added to this solution, then the solution was stirred at room temperature overnight. After completion of the reaction, the reaction mixture was concentrated under reduced pressure, and then washed with ethyl acetate in a separating funnel. By concentrating the organic layer under reduced pressure, compound (6) (partial linker B) [compound (6) in the above-described synthesis route] (3.6 g) was obtained (yield; quantitative).

(3) Introduction of the Linkers
(i) Introduction of the Partial Linker A (the 5th Step)

5-Iodo-2'-deoxycytidine [compound (7) in the above-described synthesis route] (produced by Wako Pure Chemical Industries) (1.0 g) was suspended in acetonitrile (30 mL), and after addition of N,O-bis(trimethylsilyl)acetamide (TMS-Acetamide) (3 mL) under Ar gas atmosphere, the reaction mixture was stirred under reflux for 2 hours. After cooling the reaction mixture to room temperature, bis(acetonitrile) dichloropalladium (II) [$PdCl_2(CH_3CN)_2$] (40 mg) and the partial linker A [the compound of (3) in the above-described synthesis route] (2 g) was added, and the reaction mixture was further stirred at 50-60° C. for 20 hours. After the reaction was completed, the reaction mixture was concentrated under reduced pressure. The residue was purified through silica gel column (eluent; $CHCl_3$:MeOH=9:1), then crystallized from diethyl ether solution, and thus the 2'-deoxycytidine derivative [compound (8) in the above-described synthesis route] (720 mg) was obtained (yield; 67.3%).

(ii) Detrifluoroacetylation (Tfa) (the 6th Step)

After dissolving the 2'-deoxycytidine derivative [compound (8) in the above-described synthesis route] (500 mg) in EtOH (10 mL) and adding thereto 25% aqueous ammonia (25 mL), the mixture was stirred at room temperature for 4 hours. After completion of the reaction, the reaction mixture was concentrated under reduced pressure. The residue was purified through ODS column chromatography (eluent; 5% MeOH), and thus the 2'-deoxycytidine derivative [compound (9) in the above-described synthesis route] (190 mg) was obtained (yield; 50.9%).

(iii) Introduction of the Partial Linker B (the 7th Step)

After dissolving the 2'-deoxycytidine derivative [compound (9) in the above-described synthesis route] (190 mg) in N,N-dimethylformamide (DMF) (4 mL) and adding the partial linker B [compound (6) in the above-described synthesis route] (330 mg), the mixture was stirred at room temperature overnight. After completion of the reaction, the reaction mixture was concentrated under reduced pressure, and then the residue was purified through silica gel column (eluent; $CHCl_3$:MeOH:AcOH=80:20:5). Further purification was carried out through ODS column chromatography (eluent; 20% MeOH), and the 2'-deoxycytidine derivative [compound (10) in the above-described synthesis route] (169 mg) was obtained (yield; 51.2%).

(4) Triphosphorylation of Mononucleoside
(i) Preparation of triphosphorylation reagent of 0.5 M tris(tri-n-butylammonium)pyrophosphate [tris(TBAPP)]

Aqueous solution of sodium pyrophosphate decahydrate (6.7 g/100 mL) was loaded on a Dowex 50 W×8 (H+ form) (100 cm$^3$) column and eluate (pyrophosphoric acid solution) was dropped directly into aqueous EtOH solution (50 mL) containing tributylamine (10.6 mL). After stirring for 10 minutes, the eluate was concentrated under reduced pressure, then EtOH (30 mL×twice), toluene (30 mL×3 times), N,N-dimethylformamide (DMF) (20 mL×twice) were sequentially added to the residue, and concentration was repeated each time under reduced pressure. After adjusting the volume to 30 mL with DMF, MS4A was added and dehydrated overnight, and thus 0.5 M tris(TBAPP) solution was obtained.

(ii) Triphosphorylation (the 8th Step)

After dissolving the 2'-deoxycytidine derivative [compound (10) in the above-described synthesis route] (147 mg, 0.3 mmol) in triethyl phosphate [(EtO)$_3$PO] (1.4 mL) and adding phosphorous oxychloride (27 µL+24 µL) thereto, the mixture was stirred in a low-temperature chamber for 4 hours. To this reaction mixture, the above obtained 0.5 M tris (TBAPP) (4 mL) was added and stirred in a low-temperature chamber for 2 hours. After that, 7% aqueous triethylamine (Et$_3$N) solution (7 mL) was added and the reaction mixture was further stirred overnight. After the reaction was completed, the reaction mixture was washed with diethyl ether and purified through the DEAE-TOYOPEARL column (eluent; water→0.2 M TEAB gradient). Subsequently, the concentrated residue was dissolved in 25% aqueous ammonia (30 mL), and stirred in a low-temperature chamber for all night. After completion of the reaction, ammonia was distilled away under reduced pressure, and the residue was freeze-dried. Thus, the 2'-dCTP-amino linker derivative [compound (11) in the above-described synthesis route] (130 mg) was obtained (HPLC purity; 95.8%, content; 77.3%).

(5) Labeling of Mononucleotide (the 9th Step)

After dissolving the 2'-dCTP-amino-linker derivative [the compound (11) in the above-described synthesis route] (2.8 mg) in ion-exchanged water (150 µL), a solution of Dy547-NHS-ester (produced by Dyomics GmbH) [compound of (12a) in the above-described synthesis route] in DMF (1 mg/100 µL) was added 5 times, and the mixture was stirred at room temperature overnight. After completion of the reaction, the reaction mixture was concentrated under reduced pressure, then subjected to purification through Wakosil 50C$^{18}$ column (eluent; 5% MeOH), subsequently through DEAE-TOYOPEARL 650M column (eluent; 0.2 M TEAB). The concentrated residue was freeze-dried, and thus the fluorescence labeled 2'-dCTP derivative [compound (13a) (Dy547-dCTP) in the above-described synthesis route: the mononucleotide labeled with the labeling substance (2) involved in the present invention] (2.5 mg) was obtained.

In addition, the same procedure was carried out as described above, except for using Dy647-NHS-ester (produced by Dyomics GmbH) [the compound (12b) in the above-described synthesis route] instead of Dy547-NHS-ester, and the fluorescence labeled 2'-dCTP derivative [the compound (13b) (Dy647-dCTP) in the above-described synthesis route: the mononucleotide labeled with the labeling substances (1) involved in the present invention] (2.5 mg) was obtained.

Synthesis Example 2

Synthesis of Labeled Mononucleotides (fluorescence labeled 2'-deoxyuridine-5'-triphosphate derivatives)

The mononucleotide (2'-deoxyuridine-5'-triphosphate) which was labeled with the labeling substance (1) involved in the present invention and the mononucleotide (2'-deoxyuridine-5'-triphosphate) which was labeled with the labeling substance (2) involved in the present invention were synthesized as follows according to the synthesis routes as described above, respectively.

(1) Introduction of the Linkers (i) Introduction of the Partial Linker A (the 5th Step)

5-Iodo-2'-deoxyuridine [compound (14) in the above-described synthesis route] (produced by Wako Pure Chemical Industries) (3.0 g) was suspended in N,N-dimethylformamide (DMF) (25 mL). Under Ar gas atmosphere, a tri-2-furylphosphine (TFP) (80 mg), tris(dibenzylideneacetone) dipalladium(0) [Pd$_2$(dba)$_3$] (160 mg) and the partial linker A [compound of (3) in the above-described synthesis route] (4.5 g) was added to the suspension, and the mixture was stirred at room temperatures for 20 hours. After completion of the reaction, the reaction mixture was subjected to concentration under reduced pressure and crystallization from ethanol. Thus, the 2'-deoxyuridine derivative [compound (15) in the above-described synthesis route] (2.4 g) was obtained (yield; 80.5%).

(ii) Detrifluoroacetylation (Tfa) (the 6th Step)

After dissolving the 2'-deoxyuridine derivative [the compound (15) in the above-described synthesis route] (1.6 g) in MeOH (20 mL) and adding 25% aqueous ammonia (25 mL) thereto, the mixture was stirred at room temperature for 4 hours. After completion of the reaction, the reaction mixture was concentrated under reduced pressure and crystallized from ethanol. Thus, the 2'-deoxyuridine derivative [compound (16) in the above-described synthesis route] (1.0 g) was obtained (yield; 82.6%).

(iii) Introduction of the Partial Linker B (the 7th Step)

After dissolving the 2'-deoxyuridine derivative [compound (16) in the above-described synthesis route] (700 mg) in N,N-dimethylformamide (DMF) (10 mL) and adding the partial linker B [compound (6) in the above-described synthesis route] (1 g), the mixture was stirred at room temperature overnight. After completion of the reaction, the reaction mixture was concentrated under reduced pressure, and then the residue was purified through silica gel column (eluent; CHCl$_3$:MeOH:AcOH=80:20:5). Thus, the 2-deoxyuridine derivative [compound (17) in the above-described synthesis route] (870 mg) was obtained (yield; 71.3%).

(2) Triphosphorylation of Mononucleoside (i) Triphosphorylation (the 8th Step)

After dissolving the 2'-deoxyuridine derivative [compound (17) in the above-described synthesis route] (147 mg, 0.3 mmol) in triethyl phosphate [(EtO)$_3$PO] (1.4 mL) and adding phosphorous oxychloride (27 µL+24 µL) thereto, the mixture was stirred in a low-temperature chamber for 4 hours. To this reaction mixture, the above obtained 0.5 M tris(tri-n-butylammonium)pyrophosphate [tris(TBAPP)] (4 mL) was added and the reaction mixture was stirred in a low-temperature chamber for 2 hours. After that, 7% aqueous triethylamine solution (7 mL) was added and the reaction mixture was further stirred overnight. After the reaction was completed, the reaction mixture was washed with diethyl ether and purified through the DEAE-TOYOPEARL column (eluent; water→0.2 M TEAB gradient). Subsequently, the concentrated residue was dissolved in 25% aqueous ammonia (30 mL), and stirred in a low-temperature chamber overnight. After completion of the reaction, ammonia was distilled away under reduced pressure, and the residue was freeze-dried. Thus, the 2'-dUTP-amino linker derivative [compound (18) in the above-described synthesis route] (130 mg) was obtained (HPLC purity; 96.3%, content; 42.0%).

(3) Labeling of Mononucleotide (the 9th Step)

After dissolving the 2'-dUTP-amino-linker derivative [compound (18) in the above-described synthesis route] (1.4 mg) in ion-exchanged water (150 µL), a solution of Dy547-NHS-ester (produced by Dyomics GmbH) [compound of (12a) in the above-described synthesis route] in DMF (1 mg/100 µL) was added thereto 5 times, and the mixture was stirred at room temperature overnight. After completion of the reaction, the reaction mixture was concentrated under reduced pressure, then subjected to purification through Wakosil 50C$^{18}$ column (eluent; 5% MeOH), subsequently through DEAE-TOYOPEARL 650M column (eluent; 0.2 M TEAB). The concentrated residue was freeze-dried, and thus the fluorescence labeled 2'-dUTP derivative [compound (19a) (Dy547-dUTP) in the above-described synthesis route: the mononucleotide labeled with the labeling substance (2) involved in the present invention] (2.2 mg) was obtained.

In addition, the same procedure was carried out as described above, except for using Dy647-NHS-ester (produced by Dyomics GmbH) [compound (12b) in the above-described synthesis route] instead of Dy547-NHS-ester, and the fluorescence labeled 2'-dUTP derivative [compound (19b) (Dy647-dUTP) in the above-described synthesis route: the mononucleotide labeled with the labeling substances (1) involved in the present invention] (1.8 mg) was obtained.

Example 1

CGH Analysis Using BAC Array

Using the genomic DNA derived from normal female as a test genomic DNA fragment and the genomic DNA derived from normal male as a control genomic DNA fragment, the CGH analysis by BAC array was carried out.
(1) Preparation of Labeled Test Genomic DNA Fragment and Labeled Control Genomic DNA Fragment
(i) Incorporation of Labeled Nucleotide A normal Male DNA (produced by Promega Corporation) (control genomic DNA fragment) and a normal Female DNA (produced by Promega Corporation) (test genomic DNA fragment) (500 ng each) were placed separately in a tube for PCR. To each tube, 1500 µg/mL Random Octamer solution (produced by Nippon EGT Corporation) (10 µL), 250 mM MOPS (pH 7.0) (containing 25 mM MgCl$_2$ and 50 mM 2-mercaptoethanol) (10 µL) were added, and the total volume was adjusted to 39 µL using sterile water. By heating these mixed-solutions at 100° C. for 10 minutes and followed by cooling on ice for 5 minutes, the random primer was annealed to Male DNA and Female DNA, respectively. Then, after leaving them at room temperature for 5 minutes, dNTP solution [produced by Wako Pure Chemical Industries; dNTPset (containing 2 mM dATP, 2 mM dGTP, 2 mM dTTP, and 1 mM dCTP)] (5 µL) was added.

Further, to the Male DNA tube (the control genomic DNA fragment), 1 mM Dy547-dCTP [compound (13a) in the above-described synthesis route which was obtained in Synthesis Example 1] (3 µL) was added, and to the Female DNA tube (the test genomic DNA fragment), 1 mM Dy647-dCTP [compound (13b) in the above-described synthesis route which was obtained in Synthesis Example 1] (3 µL) was added. After spinning down by centrifugation, the Klenow Flagment (produced by Fermentas Inc.) (3 µL, 30 units) was added to these mixed solutions, and mixed by pipetting with care so as not to make foam from micro pipette.

After reacting at 37C.° for 16 hours, 0.5 M EDTA solution (5 µL) was added to each tube to stop the reaction.

(ii) Purification of the Labeled Genomic DNA fragment using spin column

The unreacted labeled nucleotides (Dy547-dCTP and Dy647-dCTP) which exist in the reaction mixtures of the above-mentioned (i) were removed using PCR Purification Kit (produced by Qiagen GmbH). To each tube after terminating the reaction, Binding Buffer (a buffer solution included in the PCR Purification Kit produced by Qiagen GmbH) (275 µL) was added, and mixed by pipetting.

Total amount of the mixed solution was applied to Spin Column (a column contained in the PCR Purification Kit produced by Qiagen GmbH), and centrifugal separation treatment was carried out by 6,000 rpm (3,500×g) for 2 minutes.

After flow-through was discarded, Spin Column Wash Buffer (a buffer solution included in the PCR Purification Kit produced by Qiagen GmbH) (750 µL) was added, and then centrifugal separation treatment was carried out by 6000 rpm (3,500×g) for 2 minutes. Flow-through was discarded and centrifugal separation treatment was carried out by 12,000 rpm (14,000×g) for 3 minutes.

A new microtube of 1.5 mL was set to the Spin Column, and Elution Buffer (a buffer solution included in the PCR Purification Kit produced by Qiagen GmbH) (50 µL) was added at the center of the column. After leaving the column under light shielding at room temperature for 5 minutes, centrifugal separation treatment was carried out by 12,000 rpm (14,000×g) for 3 minutes. Elution Buffer (a buffer solution included in PCR Purification Kit produced by Qiagen GmbH) (30 µL of) was added at the center of the column, and the column was left under light shielding at room temperature for 5 minutes, then centrifugal separation treatment was carried out by 12,000 rpm (14,000×g) for 3 minutes. Thus purified Dy-547 labeled Male DNA (the labeled control genomic DNA fragment) (80 µL) and purified Dy-647 labeled Female DNA (the labeled test genomic DNA fragment) (80 µL) were obtained, respectively.
(2) Hybridization Using BAC Array Using commercially available BAC array kit [MAC Array Karyo 4000, produced by Macrogen Corp.] as a BAC array, hybridization was carried out as follows:

This BAC array is the one in which 4000 clones derived from human genome BAC library was spotted (immobilized/fixed) twice on a slide glass, and, as for each clone, the sequence of both ends have been determined and the location on the chromosome has been confirmed by FISH method.
(i) Preparation of sample DNA for hybridization Dy-547 labeled Male DNA and Dy-647 labeled Female DNA obtained in the above (1) (80 µL each) were mixed, and further, Solution B (containing Cot-1 DNA) which was included in MAC Array Karyo 4000 (produced by Macrogen Corp.) (100 µL), 3 M sodium acetate (25 µL), and 100% cold ethanol (700 µL) were added and mixed. After leaving at −20° C. for 60 minutes, the mixed solution was centrifuged by 12,000 rpm (14,000×g) at 4° C. for 20 minutes. After discarding supernatant with care so as not to cause loss of pellet, 70% cold ethanol (1 mL) was added and mixed. After that, the centrifugation by 12,000 rpm (14,000×g) at 4° C. was carried out again for 5 minutes. After discarding supernatant with care so as not to cause loss of pellet, the pellet was dried under light shielding for 10 minutes. To the obtained pellet, Solution C (hybridization solution) (140 µL) and Solution D (containing yeast tRNA) (4 µL) which were included in the MAC Araay Karyo 4000 were added, and the pellet was dissolved.

The resultant solution was subjected to heat treatment at 70° C. for 10 minutes to denature the double stranded DNA (to form single strand), then allowed to pre-annealing at 37° C. for 60 minutes so that the blocking reaction of the repeated sequence by Cot-1 DNA was performed. Thus, the sample DNA (labeled sample DNA) solution for hybridization was obtained.

(ii) Pre-Hybridization

Solution C (hybridization solution) (30 μL) and Solution E (containing salmon sperm DNA) (10 μL) which are contained in the MAC Array Karyo 4000 were mixed and heated at 70° C. for 10 minutes, and then cooled on, ice for 5 minutes, to obtain the pre-hybridization solution.

The pre-hybridization solution (40 μL) was applied on the BAC array (slide glass) of MAC Array Karyo 4000, and the cover glass of the size with which all the arrays spotted could be covered was placed so that the solution might spread through the whole array. The BAC array was incubated in a humidified chamber at room temperature for 30 minutes.

The cover glass was removed at the end of incubation, the array was washed twice with sterile deionized water and once with 100% isopropanol. After that, the array was centrifuged by 2,000 rpm (780×g) for 2 minutes using a centrifugal machine for slide glass.

(iii) Hybridization

The BAC array (slide) which had been completed the pre-hybridization was set in the automated slide processing unit HybStation (produced by Genomic Solutions), and the sample DNA (labeled sample DNA) solution (120 μL) for hybridization obtained in (i) was applied. The hybridization was performed for 44 hours, by setting hybridization temperature at 37° C. and stirring the sample DNA (labeled sample DNA) solution for hybridization for every certain period of time. Washing after hybridization was also performed in the automated slide processing unit, 3 times with wash solution 1 of formamide (50%)/2×SSC, pH 7, at 46° C. for 5 minutes; 3 times with wash solution 2 (0.1% SDS/2× SSC, pH 7) at 46° C. for 10 minutes; 3 times with wash solutions 3 (0.1% NP-40/0.1M phosphate buffer, pH 7) at 46° C. for 10 minutes; and 3 times with wash solutions 4 (2×SSC, pH 7) at 46° C. for 2 minutes. After that, the BAC array (slide) was removed from the unit, and was immersed sequentially in wash-bottles filled with 70%, 85% and 100% ethanol respectively for 1 minute each, and then, centrifuged using a centrifugal machine for slide glass at 2,000 rpm (780×g) for 2 minutes, and dried.

(3) Measurement (Scanning)/Analysis

The BAC array after hybridization and washing was scanned using a scanner for microarray GenePix 4000A (produced by Axon Instruments Inc.), and the fluorescence images by the fluorescence derived from Male DNA (the control genomic DNA fragment) and by the fluorescence derived from Female DNA (the test genomic DNA fragment) on the BAC array were obtained. The obtained fluorescence image data were analyzed by the software for array CGH analysis MacViewer (produced by Macrogen Corp.), and after the fluorescence signals of Dy-547 and Dy-647 for every array spot were determined and the data were normalized, the $Log_2$ (Dy-647/Dy-547) value was calculated for every BAC clone.

(4) Results

From the $Log_2$ (Dy-647/Dy-547) value for each BAC clone, a mean value and SD of $Log_2$(Dy-647/Dy-547) in an autosomal chromosome (No. 1-22 chromosome) and an X-chromosome were calculated, respectively.

Calculation results are shown below.

Autosomal chromosome (Chr. 1-22): 0.0209 (mean) ±0.0420 (SD)

X-chromosome (Chr. X): 0.671 (mean)±0.110 (SD)

In addition, the result of $Log_2$ (Dy-647/Dy-547) value for each BAC clone plotted in the order of the chromosome number is shown in FIG. 1.

In FIG. 1, the vertical axis shows a level of increase/decrease in comparison with normal Male by a ratio of fluorescence intensity [$Log_2$ (ratio)], and a positive (+) value indicates an increase in the number of copy; and a negative (−) value indicates a decrease in the number of copy. Also, the horizontal axis indicates the chromosome number.

Comparative Example 1

CGH Analysis of BAC Array Using Conventional Fluorescent Labeling Substances

For the purpose of comparing with the present invention, the CGH analysis by BAC array was carried out using conventional fluorescent labeling substances.

(1) Preparation of Labeled Test Genomic DNA Fragment and Labeled Control Genomic DNA Fragment Preparation of Labeled Test Genomic DNA Fragment and Labeled control genomic DNA fragment was carried out by the same procedure as described in (1) of Example 1, except for using the following fluorescent labeling nucleotides (fluorescence labeled 2'-dCTP derivative).

(a) CyDye Labeled Nucleotides

Control genomic DNA fragment (Male DNA): Cy3 labeled dCTP (Cy3-dCTP, produced by PerkinElmer, Inc.)

Test genome DNA fragment (Female DNA): Cy5 labeled dCTP (Cy5-dCTP, produced by PerkinElmer, Inc.)

(b) HiLyteDye Labeled Nucleotides

Control genomic DNA fragment (Male DNA): HiLyte Fluor 555 labeled dCTP

Test genomic DNA fragment (Female DNA): HiLyte Fluor 647 labeled dCTP

It should be noted that, these HiLyteDye labeled nucleotides were prepared according to the procedure described in (5) of Synthesis Example 1 using the 2'-dCTP-amino linker derivative [compound of (11) in the above-described synthesis route] obtained in Synthesis Example 1 and commercially available fluorescent labeling substances HiLyte Fluor 555 (HiLyte 555-SE, produced by Anaspec, Inc.) and HiLyte Fluor 647 (HiLyte 647-SE, produced by Anaspec, Inc.).

(2) Hybridization Using BAC Array

Hybridization to the BAC array was performed by the same procedure as described in (2) of Example 1, except for using the following labeled test genomic DNA fragment and labeled control genomic DNA fragment obtained in the above-described (1).

(a) CyDye Labeled Test Genomic DNA Fragment and Control Genomic DNA Fragment

Labeled control genomic DNA fragment (Male DNA): Cy3 labeled Male DNA

Labeled test genomic DNA fragment (Female DNA): Cy5 labeled Female DNA (b) HiLyteDye Labeled Test Genomic DNA Fragment and Control Genomic DNA Fragment Labeled control genomic DNA fragment (Male DNA): HiLyte Fluor 555 labeled Male DNA Labeled test genomic DNA fragment (Female DNA): HiLyte Fluor 647 labeled Female DNA (3) Measurement (Scanning)/Analysis Measurement and analysis were carried out by the same procedure as described in (3) of Example 1.

It should be noted that, in the analysis, after the fluorescence signals of Cy3 and Cy5, and HiLyte Fluor 555 and HiLyte Fluor 647 were measured for every array spot and the data were normalized, $\text{Log}_2$ (Cy5/Cy3) value and $\text{Log}_2$ (HiLyte Fluor 647/HiLyte Fluor 555) value were calculated for every BAC clone, respectively.

(4) Results

From $\text{Log}_2$ (Cy5/Cy3) value for every BAC clone, a mean value and SD of $\text{Log}_2$ (Cy5/Cy3) in the autosomal chromosomes (No. 1-22 chromosome) and the X-chromosome, and also, from $\text{Log}_2$ (HiLyte Fluor 647/HiLyte Fluor 555) value, a mean value and SD of $\text{Log}_2$ (HiLyte Fluor 647/HiLyte Fluor 555) in the autosomal chromosomes (No. 1-22 chromosome) and the X-chromosome were calculated, respectively.

Calculation results are shown below, respectively.

(a) When the CyDye Labeled Test Genomic DNA Fragment and the Control Genomic DNA Fragment were Used Autosomal chromosomes (Chr. 1-22): 0.0107 (mean) ±0.0756 (SD)

X-chromosome (Chr.X): 0.619 (mean)±0.120 (SD)

(b) When the HiLyteDye Labeled Test Genomic DNA Fragment and the Control Genomic DNA Fragment were Used Autosomal chromosomes (Chr. 1-22): 0.00279 (mean) ±0.0787 (SD)

X-chromosome (Chr.X): 0.641 (mean)±0.112 (SD)

In addition, the result of $\text{Log}_2$ (Cy5/Cy3) value plotted in the order of the chromosome number for every BAC clone obtained when the Cypye labeled test genomic DNA fragment and the control genomic DNA fragment were employed is shown in FIG. 2, and the result of $\text{Log}_2$ (HiLyte Fluor 647/HiLyte Fluor 555) value plotted in the order of the chromosome number for every BAC clone obtained when the HiLytepye labeled test genomic DNA fragment and the control genomic DNA fragment were employed is shown in FIG. 3, respectively.

It should be noted that, in FIGS. 2 and 3, the vertical axis shows a level of increase/decrease in comparison with normal Male by a ratio of fluorescence intensity [$\text{Log}_2$(ratio)], and a positive (+) value indicates an increase in the number of copy; and a negative (−) value indicates a decrease in the number of copy. Also, the horizontal axis indicates the chromosome number.

Evaluation of the method of the present invention (Example 1) and the method of employing conventional fluorescent labeling substance (Comparative Example 1) was carried out on the basis of the SD of $\text{Log}_2$ (ratio) in the autosomal chromosomes and the $\text{Log}_2$(ratio) in the X-chromosome.

That is, in the autosomal chromosomes of No. 1 to No. 22 chromosome, both male and female have each 2 chromosomes, therefore, the $\text{Log}_2$ (ratio) in an autosomal chromosomes becomes theoretically 0, but practically an error arises among each clone (chromosome). This error is expressed by SD, and a smaller SD of the $\text{Log}_2$ (ratio) means a smaller variation (error) in the autosomal chromosome, and since cutoff value as appreciation of increase/decreases can be lowered, it can be deemed that highly precise measurement is possible.

On the other hand, as for the X-chromosome, since female has two and male has one, the theoretical amount of fluorescence (fluorescence intensity) becomes twice, and the $\text{Log}_2$ (ratio) in the X-chromosome becomes 1. The $\text{Log}_2$ (ratio) in this X-chromosome serves as an indicator of an increase of the chromosome, and since increase/decrease are recognized more distinctly when the $\text{Log}_2$ (ratio) in the X-chromosome is closer to one, variations of increase/decreases can be detected even if the variation is small, in other words, it can be deemed that highly sensitive detection is possible.

And so, the SD of the $\text{Log}_2$ (ratio) in the autosomal chromosome and the $\text{Log}_2$ (ratio) in the X-chromosome in the method of the present invention obtained in Example 1, and the SD of the $\text{Log}_2$ (ratio) in the autosomal chromosome and the $\text{Log}_2$ (ratio) in the X-chromosome in the method of using conventional fluorescent labeling substances obtained in Comparative Example 1 are shown in the following table.

| | Labeling substance | SD value of $\text{Log}_2$ (ratio) in the autosomal chromosome | $\text{Log}_2$ (ratio) in the X-chromosome (mean value) |
|---|---|---|---|
| Example 1 | Labeling substance (1) of the present invention Labeling substance (2) of the present invention | 0.042 | 0.671 |
| Comparative Example 1 (a) | Cy3 Cy5 | 0.0756 | 0.619 |
| Comparative Example 1 (b) | HiLyte Flour 555 HiLyte Flour 647 | 0.0787 | 0.641 |

As is clear from the above table, it turns out that the SD of the $\text{Log}_2$ (ratio) in the autosomal chromosome in the method of the present invention is 0.0420, and is very low as compared with the case (0.0756) when Cy3 and Cy5 are used and the case (0.0787) when HiLyte Fluor 555 and HiLyte Fluor 647 are used. From this fact, it turns out that the method of the present invention has little variation as compared with the conventional method and makes more highly precise measurement possible.

In addition, the $\text{Log}_2$(ratio) in the X-chromosome in the method of the present invention is 0.671, and it turns out that this value is closer to 1 than the case (0.619) when Cy3 and Cy5 are used and the case (0.641) when HiLyte Fluor 555 and HiLyte Fluor 647 are used. From this fact, it turns out that the method of the present invention can perform higher sensitive detection as compared with the conventional methods.

Example 2

Analysis of the Genomic Aberration in Hepatoma Cell by the CGH Method Using BAC Array Hepatoma cell-derived genomic DNA was used as a test genomic DNA fragment, and using the genomic DNA fragment derived from normal male as a control genomic DNA fragment, CGH analysis by BAC array was carried out.

(1) Preparation of the Labeled Test Genomic DNA Fragment and the Labeled Control Genomic DNA Fragment Preparation of Labeled Test Genomic DNA Fragment and Labeled control genomic DNA fragment was carried out by the same procedure as described in (1) of Example 1, except for having employed the following test genomic DNA fragment and control genomic DNA fragment. Test genomic DNA fragment: the genomic DNA derived from sub-cultured cells from hepatoma cell line Hep3B (liver cell-derived genomic DNA)

Control genomic DNA fragment: normal humans Male DNA (produced by Promega Corp.)

(2) Hybridization Using BAC Array

Hybridization to the BAC array was performed by the same procedure as described in (2) of Example 1, except for having employed the following labeled test genomic DNA fragment and labeled control genomic DNA fragment which were obtained in the above-described (1).

Labeled control genomic DNA fragment (Male DNA): Dy-547 labeled Male DNA

Labeled test genomic DNA fragment (genomic DNA derived from hepatic cell): Dy-647 labeled hepatoma DNA (3) Measurement (Scanning)/Analysis Measurement and analysis were carried out by the same procedure as described in (3) of Example 1.

(4) Results

The result of $\text{Log}_2$ (Dy-647/Dy-547) value for every BAC clone plotted in the order of the chromosome is shown in FIG. 4.

In FIG. 4, the vertical axis shows a level of increase/decrease in comparison with normal Male by a ratio of fluorescence intensity [$\text{Log}_2$ (ratio)], and a positive (+) value indicates an increase in the number of copy; and a negative (−) value indicates a decrease in the number of copy. Also, the horizontal axis indicates the chromosome number.

As is clear from FIG. 4, the CGH analysis patterns obtained by the method of the present invention is the same as the CGH analysis patterns obtained by the conventional method, and it turns out that the CGH analysis of hepatic cell carcinoma can be carried out satisfactorily by the methods of the present invention.

INDUSTRIAL APPLICABILITY

According to the method of the present invention, as compared with the conventional CGH method, especially with the CGH microarray method, practice of CGH analysis, namely, detection of copy number abnormality in genomic DNA can be performed more precisely with higher sensitivity.

Figure 1:
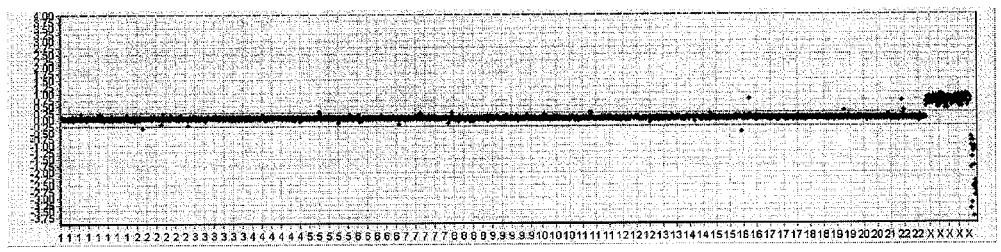
FIG. 1: This figure shows the result of $\text{Log}_2$ (Dy-647/Dy-547) value for every BAC clone obtained in Example 1, plotted in the order of the chromosome number obtained when the labeled test genomic DNA fragment (Female DNA) labeled with the labeling substance (2) (Dy-647) involved in the present invention and the labeled control genomic DNA fragment (Male DNA) labeled with the labeling substance (1) (Dy-547) involved in the present invention were employed.
Figure 2:
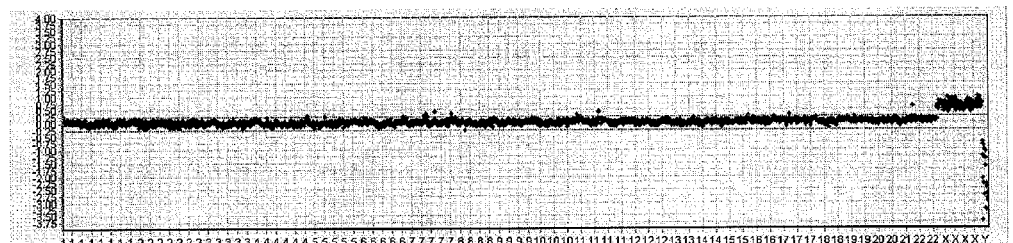
FIG. 2: This figure shows the result of $\text{Log}_2$(Cy5/Cy3) value for every BAC clone obtained in (a) of Comparative Example 1, plotted in the order of the chromosome number obtained when the Cy5 labeled test genomic DNA fragment (Female DNA) and the Cy3 labeled control genomic DNA fragment (Male DNA) were employed.
Figure 3:
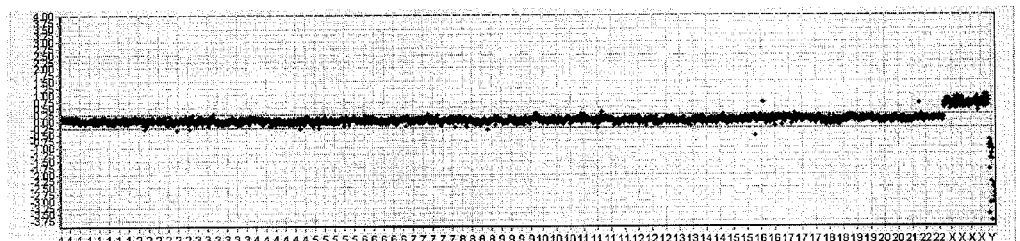
FIG. 3: This figure shows the result of $\text{Log}_2$ (HiLyte Fluor 647/HiLyte Fluor 555) value for every BAC clone obtained in (b) of Comparative Example 1, plotted in the order of the chromosome number obtained when the labeled test genomic DNA fragment (Female DNA) labeled with HiLyte Fluor 647 and the labeled control genomic DNA fragment (Male DNA) labeled with HiLyte Fluor 555 were employed.
Figure 4:
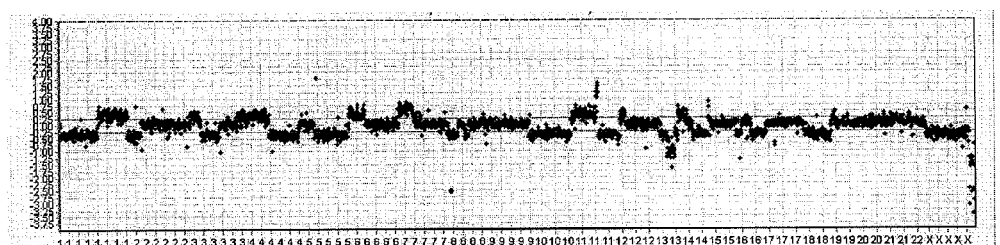
FIG. 4: This figure shows the result of $\text{Log}_2$ (Dy-647/Dy-547) value for every BAC clone obtained in Example 2, plotted in the order of the chromosome number obtained when the labeled test genomic DNA fragment (genomic DNA derived from hepatoma cell line Hep3B) labeled with the labeling substance (2) (Dy-647) involved in the present invention and the labeled control genomic DNA fragment (Male DNA) labeled with the labeling substance (1) (Dy-547) involved in the present invention were employed.

The invention claimed is:

1. A method for detecting amplification or deletion in a test genomic DNA fragment, which comprises:
   (a) labeling a test genomic DNA fragment which is a genomic DNA fragment derived from the objective cell to be inspected with either one of a labeling substance of formula (1) or a labeling substance of formula (2), and labeling a control genomic DNA fragment which is used as a standard for detecting difference from said test genomic DNA fragment with the other labeling substance,

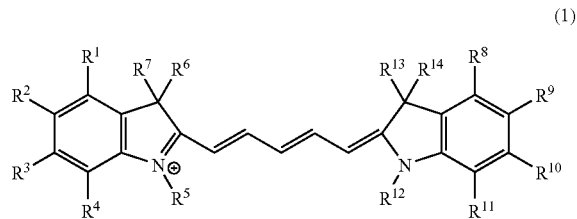

(1)

wherein $R^1$-$R^4$ and $R^8$-$R^{11}$ represent independently from each other a hydrogen atom or —$SO_3R^{15}$, wherein $R^{15}$ represents a hydrogen atom, an alkali metal atom, an organic ammonium ion or an ammonium ion, $R^5$ and $R^{12}$ represent independently from each other an alkyl group or a sulfoalkyl group, $R^6$, $R^7$, and $R^{14}$ represent independently from each other an alkyl group, and $R^{13}$ represents a carboxyalkyl group,

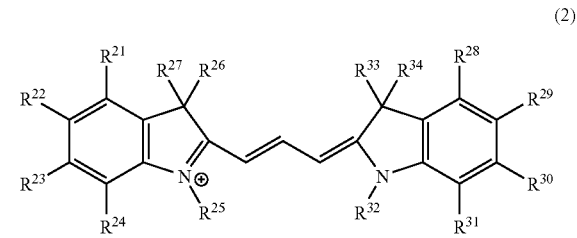

(2)

wherein $R^{21}$-$R^{24}$ and $R^{28}$-$R^{31}$ represent independently from each other a hydrogen atom or —$SO_3R^{35}$, wherein $R^{35}$ represents a hydrogen atom, an alkali metal atom, an organic ammonium ion or an ammonium ion, $R^{25}$ and $R^{32}$ represent independently from each other an alkyl group or a sulfoalkyl group, $R^{26}$, $R^{27}$ and $R^{34}$ represent independently from each other an alkyl group, and $R^{33}$ represents a carboxyalkyl group;

(b) competitively hybridizing the labeled test genomic DNA fragment and the labeled control genomic DNA fragment with a sample nucleic acid comprising a nucleotide sequence for detecting difference between the test genomic DNA fragment and the control genomic DNA fragment; and
   (c) detecting amplification or deletion in the test genomic DNA fragment by using the obtained fluorescence intensity as an indicator.

2. The method according to claim 1, wherein the sample nucleic acid is immobilized on a substrate.

3. The method according to claim 2, wherein the sample nucleic acid is derived from an artificial chromosome.

4. The method according to claim 3, wherein the artificial chromosome is a bacterial artificial chromosome (BAC) DNA.

5. The method according to claim 1, wherein the labeled test genomic DNA fragment comprises either one of the nucleotide residues of formula (3) or formula (4), and the labeled control genomic DNA fragment comprises the other nucleotide residue, wherein Q1 represents a nucleotide residue; V1 represents a linker; and W1 represents formula (1'),

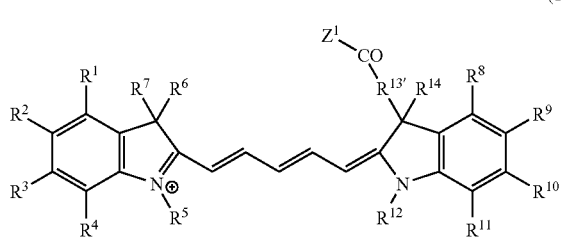

(1')

wherein $Z^1$ represents a joint for binding with V1; $R^{13'}$ represents an alkylene group; and $R^1$-$R^{12}$ and $R^{14}$ are the same as described above,

Q2-V2-W2 (4)

wherein Q2 represents a nucleotide residue; V2 represents a linker; and W2 represents the formula (2')

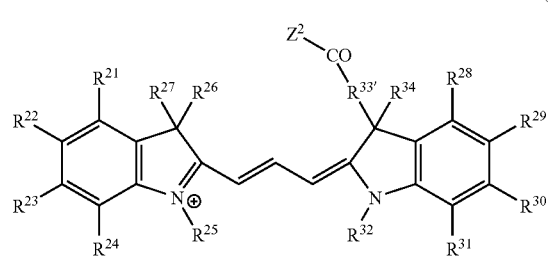

(2')

wherein $Z^2$ represents a joint for binding with V2; $R^{33'}$ represents an alkylene group; and $R^{21}$-$R^{32}$ and $R^{34}$ are the same as described above.

6. The method according to claim 5, wherein the nucleotide residue of formula (3) is a nucleotide residue of formula (3'),

Q1-E1-X1-T1-Y1-NH—W1 (3')

wherein E1 represents —CH=CH— or —C≡C—; X1 and Y1 represent independently from each other an alkylene group; T1 represents —O— or —NH—CO—; and Q1 and W1 are the same as described above; and the nucleotide residue of formula (4) is a nucleotide residue of formula (4'),

Q2-E2-X2-T2-Y2-NH—W2 (4')

wherein E2 represents —CH=CH— or —C≡C—; X2 and Y2 represent independently from each other an alkylene group; T2 represents —O— or —NH—CO—; and Q2 and W2 are the same as described above.

7. The method according to claim 1, wherein the labeling of the test genomic DNA with a labeling substance and the labeling of the control genomic DNA with a labeling substance are performed by a method selected from the group consisting of primer extension method, nick translation method, and terminal addition reaction method.

8. A kit for the method according to claim 1, which comprises:
a nucleotide residue labeled with a labeling substance of formula (1),

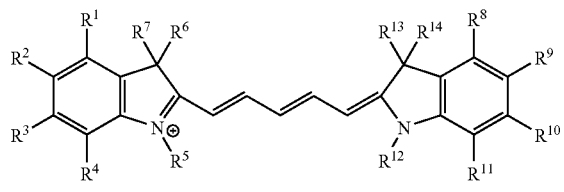

(1)

wherein $R^1$-$R^4$ and $R^8$-$R^{11}$ represent independently from each other a hydrogen atom or —$SO_3R^{15}$, wherein $R^{15}$ represents a hydrogen atom, an alkali metal atom, an organic ammonium ion or an ammonium ion, $R^5$ and $R^{12}$ represent independently from each other an alkyl group or a sulfoalkyl group, $R^6$, $R^7$ and $R^{14}$ represent independently from each other an alkyl group, and $R^{13}$ represents a carboxyalkyl group; and a nucleotide residue labeled with a labeling substance of formula (2),

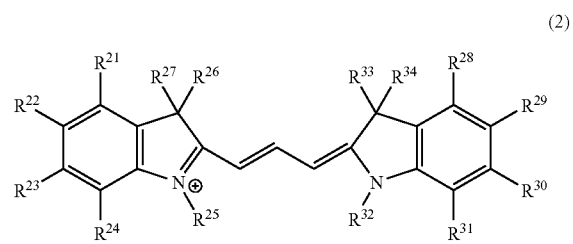

(2)

wherein $R^{21}$-$R^{24}$ and $R^{28}$-$R^{31}$ represent independently from each other a hydrogen atom or —$SO_3R^{35}$, wherein $R^{35}$ represents a hydrogen atom, an alkali metal atom, an organic ammonium ion or an ammonium ion, $R^{25}$ and $R^{32}$ represent independently from each other an alkyl group or a sulfoalkyl group, $R^{26}$, $R^{27}$ and $R^{34}$ represent independently from each other an alkyl group, and $R^{33}$ represents a carboxyalkyl group.

9. The kit according to claim 8, wherein the nucleotide residue labeled with the labeling substance of formula (1) is a nucleotide residue of formula (3),

Q1-V1-W1 (3)

wherein Q1 represents a nucleotide residue; V1 represents a linker; and W1 represents formula (1'),

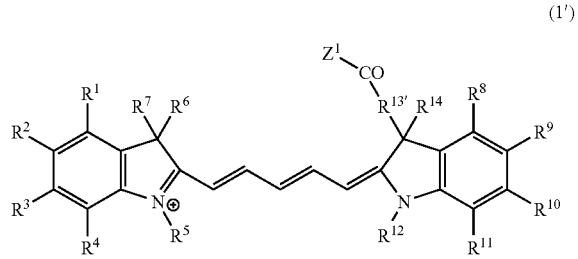

(1')

wherein $Z^1$ represents a joint for binding with V1; $R^{13'}$ represents an alkylene group; and $R^1$-$R^{12}$ and $R^{14}$ are the same as described above; and the nucleotide residue labeled with the labeling substance of formula (2) is a nucleotide residue of formula (4),

Q2-V2-W2 (4)

wherein Q2 represents a nucleotide residue; V2 represents a linker; and W2 represents formula (2'),

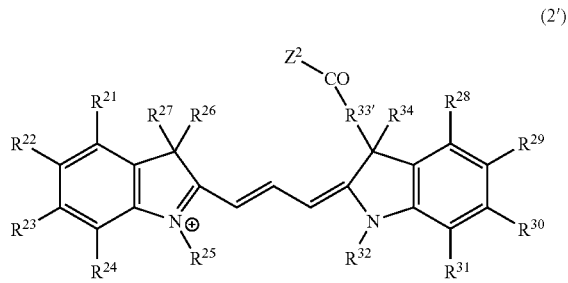

(2')

wherein $Z^2$ represents a joint for binding with V2; $R^{33'}$ represents an alkylene group; and $R^2$-$R^{32}$ and $R^{34}$ are the same as described above.

10. The kit according to claim 9, wherein the nucleotide residue of formula (3) is a nucleotide residue of formula (3'),

Q1-E1-X1-T1-Y1-NH—W1 (3')

wherein E1 represents —CH═CH— or —C≡C—; X1 represents a straight chained, branched or cyclic alkylene group having 1-6 carbon atoms; Y1 represents a straight chained, branched or cyclic alkylene group having 2-8 carbon atoms; T1 represents —O— or —NH—CO—; and Q1 and W1 are the same as described above; and the nucleotide residue of formula (4) is a nucleotide residue of formula (4'),

Q2-E2-X2-T2-Y2-NH—W2 (4')

wherein E2 represents —CH═CH— or —C≡C—; X2 represents a straight chained, branched or cyclic alkylene group having 1-6 carbon atoms; Y2 represents a straight chained, branched or cyclic alkylene group having 2-8 carbon atoms; T2 represents —O— or —NH—CO—; and Q2 and W2 are the same as described above.

11. The kit according to claim 8, further comprising at least one component selected from the group consisting of a primer for random primer method, dATP, dGTP, dCTP, dTTP and/or dUTP, and Klenow Fragment.

12. The kit according to claim 8, further comprising an instruction manual describing the use of the nucleotide residue labeled with a labeling substance of formula (1) or the nucleotide residue labeled with a labeling substance of formula (2) in a method for detecting amplification or deletion in a test genomic DNA fragment, which method comprises (a) labeling a test genomic DNA fragment which is a genomic DNA fragment derived from the objective cell to be inspected with either one of a labeling substance of formula (1) or a labeling substance of formula (2), and utilizing either the nucleotide residue labeled with a labeling substance of formula (1) or the nucleotide residue labeled with a labeling substance of formula (2) as a control genomic DNA fragment which is used as a standard for detecting difference from said test genomic DNA fragment with the other labeling substance, (b) competitively hybridizing the labeled test genomic DNA fragment and the labeled control genomic DNA fragment with a sample nucleic acid comprising a nucleotide sequence for detecting difference between the test genomic DNA fragment and the control genomic DNA fragment; and (c) detecting amplification or deletion in the test genomic DNA fragment by using obtained fluorescence intensity as an indicator.

* * * * *

UNITED STATES PATENT AND TRADEMARK OFFICE
CERTIFICATE OF CORRECTION

PATENT NO. : 8,105,770 B2
APPLICATION NO. : 12/524267
DATED : January 31, 2012
INVENTOR(S) : Amano et al.

It is certified that error appears in the above-identified patent and that said Letters Patent is hereby corrected as shown below:

In the claims:

Claim 9, at column 53, line 22 "$R^2$-$R^{32}$" should read "$R^{21}$-$R^{32}$"

Signed and Sealed this
Tenth Day of April, 2012

David J. Kappos
*Director of the United States Patent and Trademark Office*